United States Patent
Good et al.

(10) Patent No.: US 10,294,244 B2
(45) Date of Patent: May 21, 2019

(54) 2,3-DIHYDRO-THIAZOLO[3,2-A]PYRIDIN-5-ONE DERIVATIVES, INTERMEDIATES THEREOF, AND THEIR USE AS ANTIBACTERIAL AGENTS

(71) Applicant: Quretech Bio AB, Umeå (SE)

(72) Inventors: James Arthur Dudley Good, Durham (GB); Anna Martina Kulén, Umeå (SE); Klas Fredrik Almqvist, Umeå (SE); Andrew Gerard Cairns, Umeå (SE); John Fritiof Pontén, Askim (SE)

(73) Assignee: QURETECH BIO AB, Umeå (SE)

( * ) Notice: Subject to any disclaimer, the term of this patent is extended or adjusted under 35 U.S.C. 154(b) by 0 days.

(21) Appl. No.: 15/526,478

(22) PCT Filed: Nov. 13, 2015

(86) PCT No.: PCT/EP2015/076578
§ 371 (c)(1),
(2) Date: May 12, 2017

(87) PCT Pub. No.: WO2016/075296
PCT Pub. Date: May 19, 2016

(65) Prior Publication Data
US 2017/0334931 A1 Nov. 23, 2017

(30) Foreign Application Priority Data
Nov. 13, 2014 (SE) ........................ 1451358

(51) Int. Cl.
*C07D 513/04* (2006.01)
(52) U.S. Cl.
CPC .................................. *C07D 513/04* (2013.01)
(58) Field of Classification Search
CPC ................................................... C07D 513/04
See application file for complete search history.

(56) References Cited

FOREIGN PATENT DOCUMENTS

| WO | WO 01/36426 | 5/2001 |
| WO | WO 2005/102330 | 11/2005 |
| WO | WO 2014/185853 | 11/2014 |

OTHER PUBLICATIONS

Chorell "Mapping pilicide anti-virulence effect in *Escherichia coli*, a comprehensive structure—activity study." Bioorganic & Medicinal Chemistry 20 (2012) 3128-3142.*
Nelson, "Screening for Chlamydial Infection" Am J Prev Med 2001;20(3S) 95-107.*
Wislicenus, J. "Adolph Strecker's Short Textbook of Organic Chemistry" 1881, Spottiswoode: London, pp. 38-39.*
International Search Report and Written Opinion were dated Dec. 17, 2015 by the International Searching Authority for International Application No. PCT/EP2015/076578, which was filed on Nov. 13, 2015 and published as WO 2016/075296 on May 19, 2016 (Applicant—Quretech Bio AB) ( 10 pages).
Chorell, Erik et al: "Mapping pilicide anti-virulence effect in *Escherichia coli*, a comprehensive structure-activity study," Bioorg Med Chem., (2012); 20(9):3128-42.
Engström , P. et al., "A 2-Pyridone-Amide Inhibitor Targets the Glucose Metabolism Pathway of Chlamydia trachomatis," mBio, (2015) 6(1): e02304-02314.

* cited by examiner

*Primary Examiner* — David K O'Dell
(74) *Attorney, Agent, or Firm* — Ballard Spahr LLP

(57) ABSTRACT

The disclosure relates to certain novel substituted ring-fused thiazolino 2-pyridines of Formula I, to processes for preparing such compounds, to their use in treating a bacterial infection such as *Chlamydia* infection, to methods for their therapeutic use and to pharmaceutical compositions containing them.

23 Claims, No Drawings

2,3-DIHYDRO-THIAZOLO[3,2-A]PYRIDIN-5-ONE DERIVATIVES, INTERMEDIATES THEREOF, AND THEIR USE AS ANTIBACTERIAL AGENTS

CROSS-REFERENCE TO RELATED APPLICATIONS

The present application is a U.S. National Phase Application of International Application No. PCT/EP2015/076578, filed Nov. 13, 2015, which claims priority to Swedish Patent Application No. 1451358-4, filed Nov. 13, 2014, each of which are hereby incorporated by reference in their entirety.

TECHNICAL FIELD

The present disclosure relates to certain novel substituted ring-fused thiazolino 2-pyridones, to processes for preparing such compounds, to their use in treating *Chlamydia* infections, to methods for their therapeutic use and to a pharmaceutical composition containing any such compound.

BACKGROUND

*Chlamydia* infection is a common sexually transmitted infection in humans caused by the bacterium *Chlamydia trachomatis*. Both men and women may be infected, and symptoms include pain when urinating, heavier periods than normal in women and pain in the testicles in men. Commonly, however, no symptoms are noticeable or symptoms appear only after the infection has spread significantly. If left untreated, there is a considerable risk that the infected person not only passes the infection on to other people but also will suffer from severe complications.

In women, an untreated chlamydia infection can spread to the cervix, uterus and womb and cause pelvic inflammatory disease (PID). PID is a major cause of infertility, miscarriage and ectopic pregnancy. Further, the infant of a chlamydia infected pregnant woman may develop chlamydia-related conjunctivitis and pneumonia.

In men, an untreated chlamydia infection may lead to urethritis (i.e. inflammation of the urethra), orchitis (i.e. swollen testicles), reactive arthritis, and infertility.

Due to the serious consequences of chlamydia infection health care authorities in many countries recommend and arrange for screening of parts of the population considered at risk for infection. When detected, *Chlamydia trachomatis* infection can mostly be effectively cured with antibiotics such as azithromycin, doxycycline, erythromycin, amoxicillin or ofloxacin.

However, there is increasing concern about antibiotic resistance, i.e. the fact that some bacteria cannot be controlled or killed by antibiotics, which is considered a major threat to public health.

PCT/SE2014/050584 discloses substituted ring-fused thiazolino 2-pyridones useful in the treatment of *Chlamydia* infection.

"A 2-Pyridone-Amide Inhibitor Targets the Glucose Metabolism Pathway of *Chlamydia trachomatis*" (mBio vol. 6 no. 1, e02304-14 (doi:10.1128/mBio.02304-14) Patrik Engström et al 2015, discloses substituted ring-fused thiazolino 2-pyridones useful in the treatment of *Chlamydia* infection. The compound named 7-(naphthalen-1-ylmethyl)-8-cyclopropyl-5-oxo-N-phenyl-5H-[1,3]thiazolo[3,2-a]pyridine-3-carboxamide (KSK 120) is identified as a lead compound, and is said to target glucose metabolism of *Chlamydia trachomatis* by targeting the inner membrane localized hexose-phosphate transporter.

There is a need for alternative treatments of bacterial infections such as *Chlamydia* infection that may be used alone or in conjunction with any existing treatment.

It is an object of the present disclosure to provide compounds useful in the treatment, prevention and/or alleviation of bacterial infections such as *Chlamydia* infection.

SUMMARY

In accordance with the present disclosure there is provided a compound of Formula I: The present disclosure provides compounds of Formula I

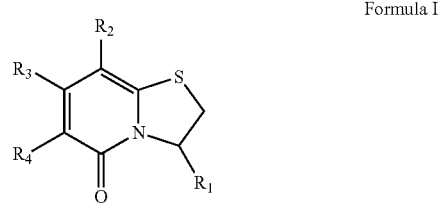

Formula I or a pharmaceutically acceptable salt thereof,
wherein
R$_1$ is selected from the group consisting of
a) C(O)NR$_5$R$_6$,
b) C(O)OH,
c) C(O)SO$_2$R$_8$,
and
d)

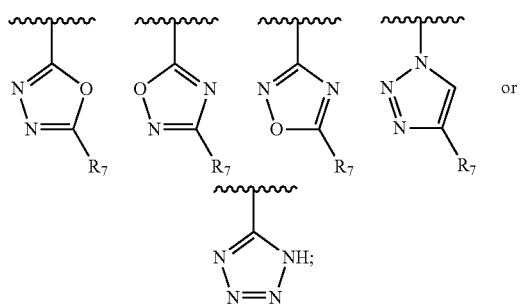

R$_2$ is selected from the group consisting of
a) OH,
b) NZ$_1$Z$_2$,
c) C$_1$-C$_4$alkoxy substituted with 0, 1, 2 or 3 substituents independently selected from the group consisting of F and Cl,
d) cyclopropoxy, cyclopropylmethoxy, phenyloxy, 2-pyridinyloxy or 4-pyridinyloxy each independently substituted with 0, 1, 2 or 3 substituents selected from the group consisting of F, Cl, methyl, ethyl, n-propyl, isopropyl, trifluoromethyl, methoxy, CH$_3$SO$_2$O and phenylSO$_2$O,
e) C$_1$-C$_3$alkylthio, C$_1$-C$_3$alkylS(O) and C$_1$-C$_3$alkylS(O)$_2$, phenylthio, phenylS(O) or phenylS(O)$_2$ each independently substituted with 0, 1, 2 or 3 substituents selected from the group consisting of F, Cl, methoxy, methyl and trifluoromethyl,
f) 2-pyridinylS(O)$_2$ substituted with 0, 1 or 2 substituents in positions 3, 4 or 5 independently selected from the group consisting of F, Cl, methoxy, methyl and trifluoromethyl, g) 4-pyridinylS(O)$_2$ substituted with 0, 1 or 2 substituents in positions 2, 3 or 5 independently selected from the group consisting of F, Cl, methoxy, methyl and trifluoromethyl,
h) Cl or F, and
i) CF$_3$;

R$_3$ is selected from the group consisting of
a) CX$_1$X$_2$phenyl, CH$_2$Ophenyl, CX$_1$X$_2$-(2)-pyridyl, CX$_1$X$_2$-(3)-pyridyl or CX$_1$X$_2$-(4)-pyridyl, each independently substituted with 0, 1, 2 or 3 substituents selected from the group consisting of F, Cl, methoxy, trifluoromethyl and methyl,
b) 1,3-dioxa-5-indanyl-methylene,
c) 1-naftyl-methylene or 1-naftyl-4-methyl-methylene, and
d) 7-thiabicyclo[4.3.0]nona-1,3,5,8-tetraen-9-yl-methylene;

R$_4$ is selected from the group consisting of:
a) hydrogen, and
b) NY$_1$Y$_2$.

The following applies in the above definitions.
R$_5$ represents hydrogen or C$_1$-C$_6$alkyl, or
R$_5$ represents phenyl, 2-pyridinyl or 4-pyridinyl each independently substituted with 0, 1, 2 or 3 substituents selected from the group consisting of F, Cl, methoxy, methyl and trifluoromethyl.
R$_6$ represents hydrogen, C$_1$-C$_4$alkyl or C$_1$-C$_6$cycloalkyl.
R$_7$ represents phenyl or 2-pyridinyl each independently substituted with 0, 1 or 2 substituents selected from the group consisting of F, Cl, methoxy, methyl and trifluoromethyl.
R$_8$ represents C$_1$-C$_3$alkyl, phenyl, 2-pyridinyl or 4-pyridinyl each independently substituted with 0, 1 or 2 substituents selected from the group consisting of F, Cl, methoxy, methyl and trifluoromethyl.
X$_1$ and X$_2$ each independently represents hydrogen, OH, halogen, oxo or NH$_2$.
Y$_1$ and Y$_2$ each independently represents hydrogen, methyl, CH$_3$S(O)$_2$ or C(O)CH$_3$, or Y$_1$ and Y$_2$ together form CH$_2$CH$_2$CH$_2$CH$_2$ or CH$_2$CH$_2$CH$_2$CH$_2$CH$_2$.
Z$_1$ and Z$_2$ each independently represents hydrogen, C$_1$-C$_4$alkyl, C$_3$-C$_5$cycloalkyl, C(O)CH$_3$, C(O)OCH$_3$, CH$_3$S(O)$_2$ or phenylS(O)$_2$, or Z$_1$ and Z$_2$ together form CH$_2$CH$_2$CH$_2$, CH$_2$CH$_2$CH$_2$CH$_2$ or CH$_2$CH$_2$CH$_2$CH$_2$CH$_2$.

There is also provided a compound as described herein such as a compound of Formula I, any of its stereoisomers, any mixture of its stereoisomers, or a pharmaceutically acceptable salt thereof, for use as a medicament in therapy.

There is also provided a pharmaceutical composition comprising a therapeutically effective amount of a compound as described herein such as Formula I as defined herein, any of its stereoisomers, or a pharmaceutically acceptable salt thereof, and a pharmaceutically acceptable adjuvant, diluent or carrier.

There is also provided a compound as described herein such as a compound of Formula I, any of its stereoisomers, any mixture of its stereoisomers, or a pharmaceutically acceptable salt thereof, for use in the treatment, prevention and/or alleviation of a bacterial infection.

There is also provided a use of a compound as described herein such as a compound of Formula I, any of its stereoisomers, any mixture of its stereoisomers, or a pharmaceutically acceptable salt thereof, for the manufacture of a medicament for use in the treatment, prevention and/or alleviation of a bacterial infection.

There is also provided a method of treatment, prevention and/or alleviation of a bacterial infection comprising administering to a mammal, including a human, in need thereof an effective amount of a compound as described herein such as a compound of Formula I, any of its stereoisomers, any mixture of its stereoisomers, or pharmaceutically acceptable salt thereof.

DESCRIPTION

The present disclosure provides compounds of Formula I:

Formula I or a pharmaceutically acceptable salt thereof,
wherein
R$_1$ is selected from the group consisting of
a) C(O)NR$_5$R$_6$,
b) C(O)OH,
c) C(O)SO$_2$R$_8$,
and
d)

R$_2$ is selected from the group consisting of
a) OH,
b) NZ$_1$Z$_2$,
c) C$_1$-C$_4$alkoxy substituted with 0, 1, 2 or 3 substituents independently selected from the group consisting of F and Cl,
d) cyclopropoxy, cyclopropylmethoxy, phenyloxy, 2-pyridinyloxy or 4-pyridinyloxy each independently substituted with 0, 1, 2 or 3 substituents selected from the group consisting of F, Cl, methyl, ethyl, n-propyl, isopropyl, trifluoromethyl, methoxy, CH$_3$SO$_2$O and phenylSO$_2$O,
e) C$_1$-C$_3$alkylthio, C$_1$-C$_3$alkylS(O) and C$_1$-C$_3$alkylS(O)$_2$, phenylthio, phenylS(O) or phenylS(O)$_2$ each independently substituted with 0, 1, 2 or 3 substituents selected from the group consisting of F, Cl, methoxy, methyl and trifluoromethyl,
f) 2-pyridinylS(O)$_2$ substituted with 0, 1 or 2 substituents in positions 3, 4 or 5 independently selected from the group consisting of F, Cl, methoxy, methyl and trifluoromethyl, g) 4-pyridinylS(O)$_2$ substituted with 0, 1 or 2 substituents in positions 2, 3 or 5 independently selected from the group consisting of F, Cl, methoxy, methyl and trifluoromethyl, h) Cl or F, and i) CF$_3$, R$_3$ is selected from the group consisting of a) CX$_1$X$_2$phenyl, CH$_2$Ophenyl, CX$_1$X$_2$-(2)-pyridyl, CX$_1$X$_2$-(3)-pyridyl or CX$_1$X$_2$-(4)-pyridyl, each independently substituted with 0, 1, 2 or 3 substituents selected from the group consisting of F, Cl, methoxy, trifluoromethyl and methyl, b) 1,3-dioxa-5-indanyl-methylene, c) 1-naftyl-methylene or 1-naftyl-4-methyl-methylene, and d) 7-thiabicyclo[4.3.0]nona-1,3,5,8-tetraen-9-yl-methylene;

R$_4$ is selected from the group consisting of:

a) hydrogen, and b) NY$_1$Y$_2$.

The following definitions shall apply throughout the description and the appended claims unless specifically stated otherwise.

R$_5$ represents hydrogen or C$_1$-C$_6$alkyl, or

R$_5$ represents phenyl, 2-pyridinyl or 4-pyridinyl each independently substituted with 0, 1, 2 or 3 substituents selected from the group consisting of F, Cl, methoxy, methyl and trifluoromethyl.

R$_6$ represents hydrogen, C$_1$-C$_4$alkyl or C$_1$-C$_6$cycloalkyl.

R$_7$ represents phenyl or 2-pyridinyl each independently substituted with 0, 1 or 2 substituents selected from the group consisting of F, Cl, methoxy, methyl and trifluoromethyl.

R$_8$ represents C$_1$-C$_3$alkyl, phenyl, 2-pyridinyl or 4-pyridinyl each independently substituted with 0, 1 or 2 substituents selected from the group consisting of F, Cl, methoxy, methyl and trifluoromethyl.

X$_1$ and X$_2$ each independently represents hydrogen, OH, halogen, oxo or NH$_2$.

Y$_1$ and Y$_2$ each independently represents hydrogen, methyl, CH$_3$S(O)$_2$ or C(O)CH$_3$, or Y$_1$ and Y$_2$ together form CH$_2$CH$_2$CH$_2$CH$_2$ or CH$_2$CH$_2$CH$_2$CH$_2$CH$_2$.

Z$_1$ and Z$_2$ each independently represents hydrogen, C$_1$-C$_4$alkyl, C$_3$-C$_5$cycloalkyl, C(O)CH$_3$, C(O)OCH$_3$, CH$_3$S(O)$_2$ or phenylS(O)$_2$, or Z$_1$ and Z$_2$ together form CH$_2$CH$_2$CH$_2$, CH$_2$CH$_2$CH$_2$CH$_2$ or CH$_2$CH$_2$CH$_2$CH$_2$CH$_2$.

The term "C$_1$-C$_3$alkyl" denotes a straight or branched, saturated or unsaturated, alkyl group of one to three carbon atoms. Examples of "C$_1$-C$_3$alkyl" include, but are not limited to, methyl, ethyl, vinyl, allyl, n-propyl and isopropyl.

The term "C$_1$-C$_4$alkyl" denotes a straight or branched, saturated or unsaturated, alkyl group of one to four carbon atoms. Examples of "C$_1$-C$_4$alkyl" include, but are not limited to, methyl, ethyl, vinyl, allyl, n-propyl, isopropyl, n-butyl, isobutyl, sec-butyl and tert-butyl.

The term "C$_1$-C$_6$alkyl" denotes a straight or branched, saturated or unsaturated, alkyl group of one to six carbon atoms. Examples of "C$_1$-C$_6$alkyl" include, but are not limited to, methyl, ethyl, vinyl, allyl, n-propyl, isopropyl, n-butyl, isobutyl, sec-butyl, tert-butyl, n-pentyl, 1,1-dimethylpropyl, 2,2-dimethylpropyl, 3-methylbutyl, 1-methylbutyl and 1-ethylpropyl, n-hexyl, 2-methylpentyl, 3-methylpentyl, 2,3-dimethylbutyl and 2,2-dimethylbutyl.

The term "C$_3$-C$_5$cycloalkyl" denotes a saturated or unsaturated non-aromatic monocyclic ring composed of three, four or five carbons. Examples of "C$_3$-C$_5$cycloalkyl" include, but are not limited to, cyclopropyl, cyclobutyl and cyclopentyl.

The term "C$_1$-C$_6$ cycloalkyl" denotes a saturated or unsaturated non-aromatic monocyclic ring composed of three, four, five or six carbons. Examples of "C$_3$-C$_5$cycloalkyl" include, but are not limited to, cyclopropyl, cyclobutyl, cyclopentyl, cyclohexyl.

The term "halogen" denotes fluoro, chloro, bromo and iodo.

The term "C$_1$-C$_3$alkoxy" denotes a C$_1$-C$_3$alkyl group as described herein which is linked to an oxygen. Examples of "C$_1$-C$_3$alkoxy" include, but are not limited to, methoxy, ethoxy, n-propoxy and iso-propoxy.

The term "C$_1$-C$_4$alkoxy" denotes a C$_1$-C$_4$alkyl group as described herein which is linked to an oxygen. Examples of "C$_1$-C$_4$alkoxy" include, but are not limited to, methoxy, ethoxy, n-propoxy, iso-propoxy, and butoxy.

Further, the present disclosure provides compounds of Formula I

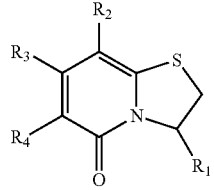

Formula I or a pharmaceutically acceptable salt thereof wherein

R$_1$ is selected from the group consisting of a) C(O)NR$_5$R$_6$, b) C(O)OH, c) C(O)SO$_2$R$_8$, and d)

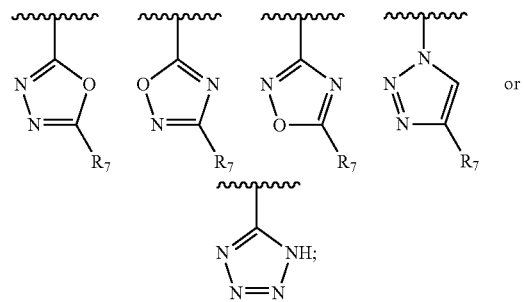

R$_2$ is selected from the group consisting of a) OH, b) NZ$_1$Z$_2$, c) C$_1$-C$_3$alkoxy substituted with 0, 1, 2 or 3 substituents independently selected from the group consisting of F and Cl, d) cyclopropoxy, phenyloxy, 2-pyridinyloxy or 4-pyridinyloxy each independently substituted with 0, 1, 2 or 3 substituents selected from the group consisting of F, Cl, methyl, ethyl, n-propyl, isopropyl, trifluoromethyl, methoxy, CH$_3$SO$_2$O and phenylSO$_2$O, e) $C_1$-$C_3$alkylthio, $C_1$-$C_3$alkylS(O) and $C_1$-$C_3$alkylS(O)$_2$, phenylthio, phenylS(O) or phenylS(O)$_2$ each independently substituted with 0, 1, 2 or 3 substituents selected from the group consisting of F, Cl, methoxy, methyl and trifluoromethyl,
f) 2-pyridinylS(O)$_2$ substituted with 0, 1 or 2 substituents in positions 3, 4 or 5 independently selected from the group consisting of F, Cl, methoxy, methyl and trifluoromethyl, and
g) 4-pyridinylS(O)$_2$ substituted with 0, 1 or 2 substituents in positions 2, 3 or 5 independently selected from the group consisting of F, Cl, methoxy, methyl and trifluoromethyl;

$R_3$ is selected from the group consisting of
a) $CX_1X_2$phenyl, $CH_2O$phenyl, $CX_1X_2$-(2)-pyridyl, $CX_1X_2$-(3)-pyridyl or $CX_1X_2$-(4)-pyridyl, each independently substituted with 0, 1, 2 or 3 substituents selected from the group consisting of F, Cl, methoxy, trifluoromethyl and methyl,
b) 1,3-dioxa-5-indanyl-methylene,
c) 1-naftyl-methylene,
and
d) 7-thiabicyclo[4.3.0]nona-1,3,5,8-tetraen-9-yl-methylene;

$R_4$ is selected from the group consisting of:
a) hydrogen,
and
b) $NY_1Y_2$.

The compound of Formula I may exist as stereoisomers such as a compound of Formula Ia or a compound of Formula Ib.

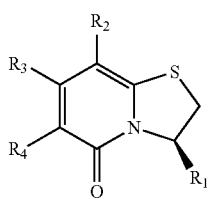

Formula Ia

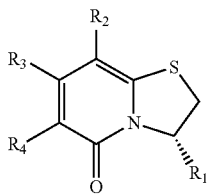

Formula Ib

It will be appreciated that the following compounds are excluded from the scope of the compound of Formula I or Formula Ia: (3R)-7-methoxy-6-[(1-naphthyl)methyl]-4-oxo-1-thia-3a-aza-3-indancarboxylic acid, (3R)-6-[(1,3-dioxa-5-indanyl)methyl]-7-methoxy-4-oxo-1-thia-3a-aza-3-indancarboxylic acid and (3R)-7-methoxy-4-oxo-6-{(7-thiabicyclo[4.3.0]nona-1,3,5,8-tetraen-9-yl)methyl}-1-thia-3a-aza-3-indancarboxylic acid.

Specific values of $R_1$, $R_2$, $R_3$ and $R_4$ of the compound of Formula I, any of its stereoisomers or any mixture of its stereoisomers, or a pharmaceutically acceptable salt thereof, will now follow. It will be understood that these values may be used with any of the definitions, claims or embodiments described herein.

The present disclosure relates to compounds of Formula I, wherein:

$R_1$ may be $C(O)NR_5R_6$. $R_5$ may be hydrogen, and $R_6$ may be phenyl or 5-chloro-2-pyridyl.
$R_1$ may be $C(O)OH$.
Further, $R_1$ may be $C(O)SO_2R_8$.
Further, $R_1$ may be

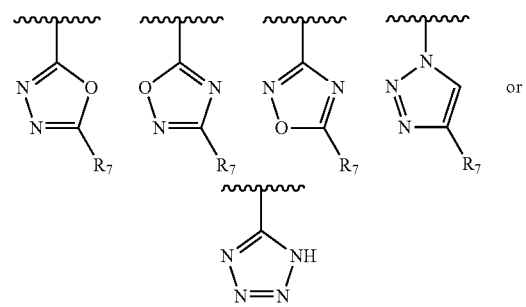

in which $R_7$ is phenyl or 2-pyridinyl each independently substituted with 0, 1 or 2 substituents independently selected from the group consisting of F, Cl, methoxy, methyl and trifluoromethyl. In an embodiment, $R_7$ may be phenyl.

For instance, $R_1$ may be selected from the group consisting of 3-phenyl-1,2,4-oxadiazol-5-y,4-Phenyl-1H-1,2,3-triazol-1-yl, 5-phenyl-1,2,4-oxadiazol-3-yl, 5-phenyl-1,3,4-oxadiazol-2-yl,anilinoformaldehyde and 5-chloro-2-pyridylamino-formaldehyde.

$R_2$ may be $C_1$-$C_3$alkoxy independently substituted with 0, 1, 2 or 3 substituents from the group consisting of F or Cl. For instance, $R_2$ may be methoxy, ethoxy or trifluoromethoxy.

Further, $R_2$ may be $NZ_1Z_2$. For instance, $R_2$ may be acetylamino, dimethylamino, methylsulfonyl, methylsulfonylamino and phenylsulfonylamino.

Further, $R_2$ may be selected from the group consisting of methoxy, ethoxy, cyclopropoxy, trifluoromethoxy, 2,2,2-trifluoroethoxy, phenoxy methylsulfonyloxy, phenylsulfonyloxy, acetylamino, dimethylamino, methylsulfonyl, methylsulfonylamino and phenylsulfonylamino.

$R_3$ may be selected from the group consisting of 1-naphthyl-methylene, 1-naphthyloxymethylene, 1,3-dioxa-5-indanyl-methylene, 2,3-xylylmethylene, 2,3-xylyloxy-methylene, 7-thiabicyclo[4.3.0]nona-1,3,5,8-tetraen-9-yl-methyl and o-tolyl-methylene.

$R_4$ may be selected from the group consisting of hydrogen, amino, acetylamino and methylsulfonylamino.

There is also provided a compound of Formula I such as a compound of Formula Ia, or a pharmaceutically acceptable salt thereof, wherein
$R_1$ is selected from the selected from the group consisting of 3-phenyl-1,2,4-oxadiazol-5-y,4-phenyl-1H-1,2,3-triazol-1-yl, 5-phenyl-1,2,4-oxadiazol-3-yl, 5-phenyl-1,3,4-oxadiazol-2-yl,anilinoformaldehyde and 5-chloro-2-pyridylamino-formaldehyde,
$R_2$ is selected from the group consisting of methoxy, cyclopropylmethoxy, trifluoromethoxy, 2,2,2-trifluoroethoxy, phenoxy methylsulfonyloxy, phenylsulfonyloxy, acetylamino, dimethylamino, methylsulfonyl, methylsulfonylamino and phenylsulfonylamino
$R_3$ is selected from the group consisting of 1-naphthyl-methylene, 1-naphthyloxymethylene, 1,3-dioxa-5-indanyl-methylene, 2,3-xylylmethylene, 2,3-xylyloxy-methylene, 7-thiabicyclo[4.3.0]nona-1,3,5,8-tetraen-9-yl-methyl and o-tolyl-methylene, and R₄ is selected from the group consisting of hydrogen, amino, acetylamino and methylsulfonylamino.

There is also provided a compound of Formula I such as a compound of Formula Ia, or a pharmaceutically acceptable salt thereof, wherein R₁ is selected from the group consisting of (3-fluoro-5-toluidino)formaldehyde, (p-toluidino)formaldehyde, anilinoformaldehyde, 3-phenyl-1,2,4-oxadiazol-5-yl, (5-chloro-2-pyridylamino)formaldehyde, 5-phenyl-1,3,4-oxadiazol-2-yl, 5-phenyl-2H-1,2,4-triazol-3-yl and carboxylic acid;

R₂ is selected from the group consisting of methoxy, chloro, isopropylamino, dimethylamino, methanesulfonylamino, methoxycarbonylamino, hydroxy, acetylamino, isobutoxy, cyclopropylmethoxy, ethoxy, allyloxy, m-(trifluoromethyl)phenylsulfonylamino, trifluoromethyl, benzoylamino, methysulfonyl, phenylsulfonylamino and amino R₃ is selected from the group consisting of 2,3-xylyl)methyl or (1-naphthyl)methyl, p-chlorophenyl)methyl, (2,3-xylyloxy)methyl or (4-methyl-1-naphthyl)methyl; and R₄ is selected from the group consisting of hydrogen and amino.

There is also provided a compound of Formula I such as a compound of Formula Ia, or a pharmaceutically acceptable salt thereof, wherein R₁ is selected from the group consisting of (3-fluoro-5-toluidino)formaldehyde, (p-toluidino)formaldehyde, anilinoformaldehyde, 3-phenyl-1,2,4-oxadiazol-5-yl, (5-chloro-2-pyridylamino)formaldehyde, and 5-phenyl-1,3,4-oxadiazol-2-yl, R₂ is selected from the group consisting of methoxy, chloro, isopropylamino, dimethylamino, methanesulfonylamino, methoxycarbonylamino, hydroxy, acetylamino, isobutoxy, cyclopropylmethoxy, ethoxy, and allyloxy;

R₃ is selected from the group consisting of (2,3-xylyl)methyl or (1-naphthyl)methyl, p-chlorophenyl)methyl, (2,3-xylyloxy)methyl and (4-methyl-1-naphthyl)methyl; and R₄ is selected from hydrogen or amino.

There is also provided a compound of Formula I such as a compound of Formula Ia, or a pharmaceutically acceptable salt thereof, wherein R₁ is selected from the group consisting of (3-fluoro-5-toluidino)formaldehyde and (p-toluidino)formaldehyde, R₂ is selected from the group consisting of methoxy, chloro, isopropylamino, dimethylamino, methanesulfonylamino, and methoxycarbonylamino;

R₃ is selected from the group consisting of (2,3-xylyl)methyl, (1-naphthyl)methyl, and p-chlorophenyl)methyl; and R₄ is selected from the group consisting of hydrogen and amino.

Examples of compounds of Formula Ia include the following compounds, or a pharmaceutically acceptable salt thereof. The compounds below may exist as the corresponding 3S stereoisomer or as a mixture of the 3R and 3S stereoisomers.

(3R)-7-Methoxy-3-(5-phenyl-1,3,4-oxadiazol-2-yl)-6-[(2,3-xylyl)methyl]-1-thia-3a-aza-4-indanone (3R)-3-[4-Phenyl-1H-1,2,3-triazol-1-yl]-5-amino-7-methoxy-6-[(2,3-xylyl)methyl]-1-thia-3a-aza-4-indanone (3R)-3-[4-Phenyl-1H-1,2,3-triazol-1-yl]-6-[(1,3-dioxa-5-indanyl)methyl]-7-methoxy-1-thia-3a-aza-4-indanone (3R)-3-[4-Phenyl-1H-1,2,3-triazol-1-yl]-7-methoxy-6-{(7-thiabicyclo[4.3.0]nona-1,3,5,8-tetraen-9-yl)methyl}-1-thia-3a-aza-4-indanone (3R)-5-Amino-7-methoxy-3-(5-phenyl-1,2,4-oxadiazol-3-yl)-6-[(o-tolyl)methyl]-1-thia-3a-aza-4-indanone (3R)-7-Methoxy-3-(5-phenyl-1,2,4-oxadiazol-3-yl)-6-[(o-tolyl)methyl]-1-thia-3a-aza-4-indanone (3R)-3-(5-Phenyl-1,2,4-oxadiazol-3-yl)-6-[(o-tolyl)methyl]-7-trifluoromethoxy-1-thia-3a-aza-4-indanone (3R)-5-Amino-7-methoxy-3-(3-phenyl-1,2,4-oxadiazol-5-yl)-6-[(2,3-xylyl)methyl]-1-thia-3a-aza-4-indanone (3R)-3-[4-Phenyl-1H-1,2,3-triazol-1-yl]-5-amino-7-methoxy-6-[(2,3-xylyloxy)methyl]-1-thia-3a-aza-4-indanone (3R)-3-[4-Phenyl-1H-1,2,3-triazol-1-yl]-5-amino-7-methoxy-6-[(1-naphthyloxy)methyl]-1-thia-3a-aza-4-indanone (3R)-3-[4-Phenyl-1H-1,2,3-triazol-1-yl]-7-methoxy-6-[(1-naphthyloxy)methyl]-1-thia-3a-aza-4-indanone {(3R)-7-Methoxy-4-oxo-6-[(2,3-xylyloxy)methyl]-1-thia-3a-aza-3-indanyl}(5-chloro-2-pyridylamino)formaldehyde {(3R)-5-Amino-7-methoxy-4-oxo-6-[(2,3-xylyloxy)methyl]-1-thia-3a-aza-3-indanyl}anilinoformaldehyde

[(3R)-5-Amino-7-cyclopropoxy-4-oxo-6-{(7-thiabicyclo[4.3.0]nona-1,3,5,8-tetraen-9-yl)methyl}-1-thia-3a-aza-3-indanyl]anilinoformaldehyde

[(3R)-7-Methoxy-4-oxo-6-{(7-thiabicyclo[4.3.0]nona-1,3,5,8-tetraen-9-yl)methyl}-1-thia-3a-aza-3-indanyl]anilinoformaldehyde {(3R)-6-[(1,3-Dioxa-5-indanyl)methyl]-7-methoxy-4-oxo-1-thia-3a-aza-3-indanyl}anilinoformaldehyde {(3R)-6-[(1,3-Dioxa-5-indanyl)methyl]-7-methoxy-4-oxo-1-thia-3a-aza-3-indanyl}(5-chloro-2-pyridylamino)formaldehyde

[(3R)-7-Methoxy-4-oxo-6-{(7-thiabicyclo[4.3.0]nona-1,3,5,8-tetraen-9-yl)methyl}-1-thia-3a-aza-3-indanyl](5-chloro-2-pyridylamino)formaldehyde {(3R)-6-[(1,3-Dioxa-5-indanyl)methyl]-7-methoxy-4-oxo-1-thia-3a-aza-3-indanyl}(5-50 chloro-2-pyridylamino)formaldehyde {(3R)-7-(Dimethylamino)-6-[(1-naphthyl)methyl]-4-oxo-1-thia-3a-aza-3-indanyl}(5-chloro-2-pyridylamino)formaldehyde {(3R)-5-Amino-7-(methylsulfonyl)-6-[(1-naphthyloxy)methyl]-4-oxo-1-thia-3a-aza-3-indanyl}anilinoformaldehyde {(3R)-6-[(1,3-Dioxa-5-indanyl)methyl]-7-(methylsulfonyloxy)-4-oxo-1-thia-3a-aza-3-indanyl}(5-chloro-2-pyridylamino)formaldehyde {(3R)-6-[(1,3-Dioxa-5-indanyl)methyl]-4-oxo-7-(phenylsulfonyloxy)-1-thia-3a-aza-3-indanyl}anilinoformaldehyde {(3R)-5-Amino-6-[(1,3-dioxa-5-indanyl)methyl]-4-oxo-7-(phenylsulfonylamino)-1-thia-3a-aza-3-indanyl}anilinoformaldehyde 1-{(3R)-3-Anilinocarbonyl-6-[(1,3-dioxa-5-indanyl)methyl]-7-(methylsulfonylamino)-4-oxo-1-thia-3a-aza-5-indanylamino}-1-ethanone 1-{(3R)-3-Anilinocarbonyl-6-[(1,3-dioxa-5-indanyl)methyl]-5-(methylsulfonylamino)-4-oxo-1-thia-3a-aza-7-indanylamino}-1-ethanone {(3R)-5-Amino-6-[(1,3-dioxa-5-indanyl)methyl]-4-oxo-7-phenoxy-1-thia-3a-aza-3-indanyl}anilinoformaldehyde {(3R)-7-Cyclopropyl-4-oxo-6-[(2,3-xylyloxy)methyl]-1-thia-3a-aza-3-indanyl}anilinoformaldehyde {(3R)-4-Oxo-7-trifluoromethoxy-6-[(2,3-xylyloxy)methyl]-1-thia-3a-aza-3-indanyl}(4-methyl-2-pyridylamino)formaldehyde {(3R)-7-Methoxy-4-oxo-6-[(2,3-xylyloxy)methyl]-1-thia-3a-aza-3-indanyl}(3-fluorotoluidino)formaldehyde and (3R)-7-(Methylsulfonyloxy)-3-(5-phenyl-2H-1,2,4-triazol-3-yl)-6-[(2,3-xylyloxy)methyl]-1-thia-3a-aza-4-indanone.

Further, the following compounds are examples of compounds of Formula I or a pharmaceutically acceptable salt thereof. The compounds below may also exist as the corresponding 3S stereoisomer or as a mixture of the 3R and 3S stereoisomers.

{(3R)-7-Cyclopropyl-4-oxo-6-[(5-quinolyl)methyl]-1-thia-3a-aza-3-indanyl}anilinoformaldehyde
{(3R)-7-Cyclopropyl-4-oxo-6-[(2,3-xylyl)methyl]-1-thia-3a-aza-3-indanyl}(p-toluidino)formaldehyde
{(3R)-6-[(p-Chlorophenyl)methyl]-7-cyclopropyl-4-oxo-1-thia-3a-aza-3-indanyl}(p-toluidino)formaldehyde and
(3R)-7-Cyclopropyl-6-[(1-naphthyl)methyl]-3-(5-phenyl-2H-1,2,4-triazol-3-yl)-1-thia-3a-aza-4-indanone.

Further, the following compounds are examples of compounds of Formula I or a pharmaceutically acceptable salt thereof. The compounds below may also exist as the corresponding 3S stereoisomer or as a mixture of the 3R and 3S stereoisomers.

{(3R)-7-Methoxy-6-[(1-naphthyl)methyl]-4-oxo-1-thia-3a-aza-3-indanyl}anilinoformaldehyde;
{(3R)-7-Methoxy-6-[(1-naphthyl)methyl]-4-oxo-1-thia-3a-aza-3-indanyl}(p-toluidino)formaldehyde;
{(3R)-7-Methoxy-4-oxo-6-[(2,3-xylyl)methyl]-1-thia-3a-aza-3-indanyl}anilinoformaldehyde;
{(3R)-7-Methoxy-4-oxo-6-[(2,3-xylyl)methyl]-1-thia-3a-aza-3-indanyl}(3-fluoro-5-toluidino)formaldehyde;
{(3R)-7-Methoxy-4-oxo-6-[(2,3-xylyl)methyl]-1-thia-3a-aza-3-indanyl}(p-toluidino)formaldehyde;
{(3R)-5-Amino-7-methoxy-6-[(1-naphthyl)methyl]-4-oxo-1-thia-3a-aza-3-indanyl}anilinoformaldehyde;
{(3R)-5-Amino-7-methoxy-4-oxo-6-[(2,3-xylyl)methyl]-1-thia-3a-aza-3-indanyl}(p-toluidino)formaldehyde;
{(3R)-5-Amino-7-methoxy-4-oxo-6-[(2,3-xylyl)methyl]-1-thia-3a-aza-3-indanyl}(3-fluoro-5-toluidino)formaldehyde;
{(3R)-5-Amino-7-methoxy-6-[(1-naphthyl)methyl]-4-oxo-1-thia-3a-aza-3-indanyl}(p-toluidino)formaldehyde;
{(3R)-7-Hydroxy-6-[(1-naphthyl)methyl]-4-oxo-1-thia-3a-aza-3-indanyl}anilinoformaldehyde;
{(3R)-7-Chloro-6-[(1-naphthyl)methyl]-4-oxo-1-thia-3a-aza-3-indanyl}anilinoformaldehyde;
{(3R)-6-[(1-Naphthyl)methyl]-4-oxo-7-(trifluoromethyl)-1-thia-3a-aza-3-indanyl}anilinoformaldehyde;
{(3R)-5-Amino-7-methoxy-4-oxo-6-[(2,3-xylyl)methyl]-1-thia-3a-aza-3-indanyl}anilinoformaldehyde;
(3R)-5-Amino-7-methoxy-3-(3-phenyl-1,2,4-oxadiazol-5-yl)-6-[(2,3-xylyl)methyl]-1-thia-3a-aza-4-indanone;
(3R)-7-Methoxy-3-(5-phenyl-1,3,4-oxadiazol-2-yl)-6-[(2,3-xylyl)methyl]-1-thia-3a-aza-4-indanone;
(3R)-7-Methoxy-3-(3-phenyl-1,2,4-oxadiazol-5-yl)-6-[(2,3-xylyl)methyl]-1-thia-3a-aza-4-indanone;
{(3R)-7-Methoxy-4-oxo-6-[(2,3-xylyloxy)methyl]-1-thia-3a-aza-3-indanyl}(5-chloro-2-pyridylamino)formaldehyde;
{(3R)-7-Methoxy-4-oxo-6-[(2,3-xylyloxy)methyl]-1-thia-3a-aza-3-indanyl}(5-chloro-2-pyridylamino)formaldehyde;
Anilino{7-(isopropylamino)-6-[(1-naphthyl)methyl]-4-oxo-1-thia-3a-aza-3-indanyl}formaldehyde;
{(3R)-7-(Dimethylamino)-6-[(1-naphthyl)methyl]-4-oxo-1-thia-3a-aza-3-indanyl}anilinoformaldehyde;
Anilino{7-(methylsulfonylamino)-6-[(1-naphthyl)methyl]-4-oxo-1-thia-3a-aza-3-indanyl}formaldehyde;
1-{3-Anilinocarbonyl-6-[(1-naphthyl)methyl]-4-oxo-1-thia-3a-aza-7-indanylamino}-1-ethanone;
{(3R)-7-(Methoxycarbonylamino)-6-[(1-naphthyl)methyl]-4-oxo-1-thia-3a-aza-3-indanyl}anilinoformaldehyde;
(3R)-7-(Cyclopropylmethoxy)-6-[(1-naphthyl)methyl]-4-oxo-1-thia-3a-aza-3-indancarboxylic acid;
(3R)-6-[(1-Naphthyl)methyl]-4-oxo-7-(trifluoromethyl)-1-thia-3a-aza-3-indancarboxylic acid;
(3R)-7-Isobutoxy-6-[(1-naphthyl)methyl]-4-oxo-1-thia-3a-aza-3-indancarboxylic acid;
(3R)-7-(Dimethylamino)-4-oxo-6-[(2,3-xylyl)methyl]-1-thia-3a-aza-3-indancarboxylic acid;
(3R)-7-(Dimethylamino)-6-[(4-methyl-1-naphthyl)methyl]-4-oxo-1-thia-3a-aza-3-indancarboxylic acid; and
(3R)-7-(Isopropylamino)-6-[(1-naphthyl)methyl]-4-oxo-1-thia-3a-aza-3-indancarboxylic acid.

Further, the following compounds are examples of compounds of Formula I or a pharmaceutically acceptable salt thereof. The compounds below may also exist as the corresponding 3S stereoisomer or as a mixture of the 3R and 3S stereoisomers.

{(3R)-7-Methoxy-6-[(1-naphthyl)methyl]-4-oxo-1-thia-3a-aza-3-indanyl}anilinoformaldehyde;
{(3R)-7-Methoxy-6-[(1-naphthyl)methyl]-4-oxo-1-thia-3a-aza-3-indanyl}(p-toluidino)formaldehyde;
{(3R)-7-Methoxy-4-oxo-6-[(2,3-xylyl)methyl]-1-thia-3a-aza-3-indanyl}anilinoformaldehyde;
{(3R)-7-Methoxy-4-oxo-6-[(2,3-xylyl)methyl]-1-thia-3a-aza-3-indanyl}(3-fluoro-5-toluidino)formaldehyde;
{(3R)-7-Methoxy-4-oxo-6-[(2,3-xylyl)methyl]-1-thia-3a-aza-3-indanyl}(p-toluidino)formaldehyde;
{(3R)-7-Chloro-6-[(1-naphthyl)methyl]-4-oxo-1-thia-3a-aza-3-indanyl}anilinoformaldehyde; and
{(3R)-6-[(1-Naphthyl)methyl]-4-oxo-7-(trifluoromethyl)-1-thia-3a-aza-3-indanyl}anilinoformaldehyde.

Further, the following compounds are examples of compounds of Formula I or a pharmaceutically acceptable salt thereof. The compounds below may also exist as the corresponding 3S stereoisomer or as a mixture of the 3R and 3S stereoisomers.

{(3R)-7-Methoxy-6-[(1-naphthyl)methyl]-4-oxo-1-thia-3a-aza-3-indanyl}anilinoformaldehyde;
{(3R)-7-Methoxy-6-[(1-naphthyl)methyl]-4-oxo-1-thia-3a-aza-3-indanyl}(p-toluidino)formaldehyde;
{(3R)-7-Methoxy-4-oxo-6-[(2,3-xylyl)methyl]-1-thia-3a-aza-3-indanyl}anilinoformaldehyde.

Further, the following compounds are examples of compounds of Formula I or a pharmaceutically acceptable salt thereof. The compounds below may also exist as the corresponding 3S stereoisomer or as a mixture of the 3R and 3S stereoisomers.

{(3R)-7-Methoxy-6-[(1-naphthyl)methyl]-4-oxo-1-thia-3a-aza-3-indanyl}(p-toluidino)formaldehyde;
{(3R)-7-Methoxy-4-oxo-6-[(2,3-xylyl)methyl]-1-thia-3a-aza-3-indanyl}(3-fluoro-5-toluidino)formaldehyde;
{(3R)-5-Amino-7-methoxy-4-oxo-6-[(2,3-xylyl)methyl]-1-thia-3a-aza-3-indanyl}(p-toluidino)formaldehyde; and
{(3R)-7-(Dimethylamino)-6-[(1-naphthyl)methyl]-4-oxo-1-thia-3a-aza-3-indanyl}anilinoformaldehyde.

The present disclosure also provides the following compounds, or a pharmaceutically acceptable salt thereof:
Anilino{7-cyclopropyl-4-oxo-6-[(2,3-xylyloxy)methyl]-1-thia-3a-aza-3-indanyl}formaldehyde;
{(3R)-7-Cyclopropyl-4-oxo-6-[(2,3-xylyl)methyl]-1-thia-3a-aza-3-indanyl}(p-toluidino)formaldehyde;
{(3R)-6-[(p-Chlorophenyl)methyl]-7-cyclopropyl-4-oxo-1-thia-3a-aza-3-indanyl}(p-toluidino)formaldehyde; and (3R)-7-Cyclopropyl-6-[(1-naphthyl)methyl]-3-(5-phenyl-2H-1,2,4-triazol-3-yl)-1-thia-3a-aza-4-indanone.

There is also provided a pharmaceutical composition comprising a therapeutically effective amount of a compound of the present disclosure such as Formula I as defined herein, any of its stereoisomers, or a pharmaceutically acceptable salt thereof, and a pharmaceutically acceptable adjuvant, diluent or carrier.

A compound of the present disclosure such as Formula I as described herein, any of its stereoisomers and any mixture of its stereoisomers, or any pharmaceutically acceptable salt thereof, may be used as a medicament in therapy.

It has been found that compounds of the present disclosure such as of Formula I as described herein are useful in the treatment, prevention and/or alleviation of a bacterial infection such as a *Chlamydia* infection. As used herein, a *Chlamydia* infection is understood to be an infection involving a *Chlamydia* species such as *Chlamydia trachomatis*. While not wishing to be bound by any specific theory, it is believed that the compounds of Formula I as described herein block the generation of *Chlamydia trachomatis* progeny by targeting the glucose metabolism of the *Chlamydia trachomatis*.

Accordingly, there is provided a compound as described herein such as a compound of Formula I, any of its stereoisomers, any mixture of its stereoisomers, or a pharmaceutically acceptable salt thereof, for use in the treatment, prevention and/or alleviation of a bacterial infection. The bacterial infection may involve gram-negative and/or gram-positive bacteria. The bacterial infection may be a *Chlamydia* infection.

There is also provided a use of a compound as described herein such as a compound of Formula I, any of its stereoisomers, any mixture of its stereoisomers, or a pharmaceutically acceptable salt thereof, for the manufacture of a medicament for use in the treatment, prevention and/or alleviation of a bacterial infection. The bacterial infection may involve gram-negative and/or gram-positive bacteria. The bacterial infection may be a *Chlamydia* infection.

Further, there is provided a method of treatment, prevention and/or alleviation of a bacterial infection comprising administering to a mammal, including a human, in need thereof an effective amount of a compound as described herein such as a compound of Formula I, any of its stereoisomers, any mixture of its stereoisomers, or pharmaceutically acceptable salt thereof. The bacterial infection may involve gram-negative and/or gram-positive bacterial. The bacterial infection may be a *Chlamydia* infection.

A suitable pharmaceutically acceptable salt of a compound of the present disclosure may be, for example, an acid-addition salt of a compound of the present disclosure which is sufficiently basic, for example, an acid-addition salt with, for example, an inorganic or organic acid, for example hydrochloric, hydrobromic, nitric, methansulphonic, sulphuric, phosphoric, trifluoroacetic, para-toluene sulphonic, 2-mesitylen sulphonic, citric, acetic, tartaric, fumaric, lactic, succinic, malic, malonic, maleic, 1,2-ethanedisulphonic, adipic, aspartic, benzenesulphonic, benzoic, ethanesulphonic or nicotinic acid. In addition a suitable pharmaceutically acceptable salt of a compound of the present disclosure, is, for example, a base-addition salt of a compound of the present disclosure which is sufficiently acidic, for example, a metal salt, for example, sodium, potassium, calcium, magnesium, zinc or aluminum, an ammonium salt, a salt with an organic base which affords a physiologically acceptable cation, which includes quartenery ammonium hydroxides, for example methylamine, ethylamine, diethylamine, trimethylamine, tert-butylamine, triethylamine, dibenzylamine, N,N-dibenzylethylamine, cyclohexylethylamine, tris-(2-hydroxyethyl)amine, hydroxyethyl diethylamine, (IR, 2S)-2-hydroxyinden-1-amine, morpholine, N-methylpiperidine, N-ethylpiperidine, imidazole, piperazine, methylpiperazine, adamantylamine, choline hydroxide, tetrabutylammonium hydroxide, tris-(hydroxymethyl)methylamine hydroxide, L-arginine, N-methyl D-glucamine, lysine or arginine.

Certain compounds of the present disclosure may exist as solvates or hydrates. It is to be understood that the present disclosure encompasses all such solvates or hydrates.

Compounds of the present disclosure may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present disclosure, whether radioactive or not, are intended to be encompassed within the scope of the present disclosure.

Compounds of the present disclosure may be administered in the form of a pro-drug. Further, the compounds of the present disclosure may be administered in combination with another therapeutic agent, for instance in the context of the treatment, prevention and/or alleviation of a bacterial infection such as a *Chlamydia* infection. Such a combination may consist or comprise of a compound of the present disclosure and an antibiotic.

Methods of Preparation

Compounds of the present disclosure may be prepared as described in Schemes 1-10. The compounds may also be prepared as described for structurally related compounds. The reactions may be carried out as in standard procedures or as described in the experimental section.

The 2-pyridone scaffold may be built up by a condensation reaction between the methyl-1,3-thiazoline-4-carboxylate and a Meldrum acid derivative under acidic catalysis at elevated temperature (Scheme 1).

Scheme 1

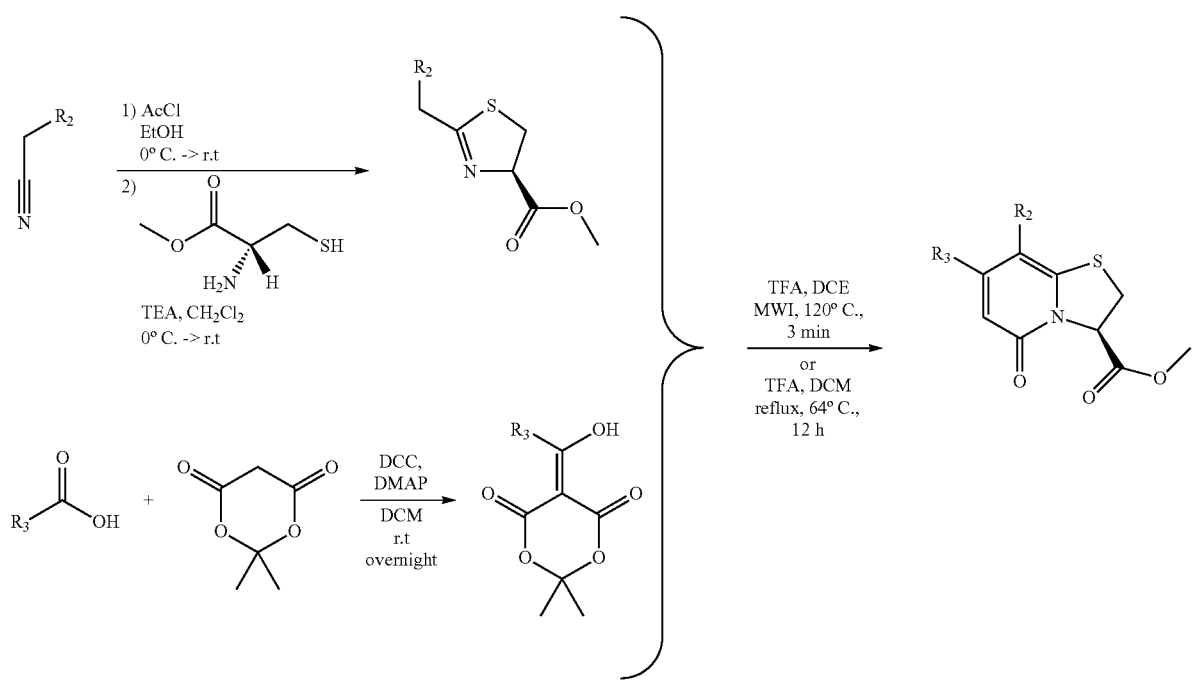

De-methylation in $R_2$ using $BBr_3$ in DCM occurs with partial hydrolysis of the methyl ester. O-alkylation followed by hydrolysis of the mixture of esters gives alkyl ethers on $R_2$ as their acid derivatives (Scheme 2).

Scheme 2

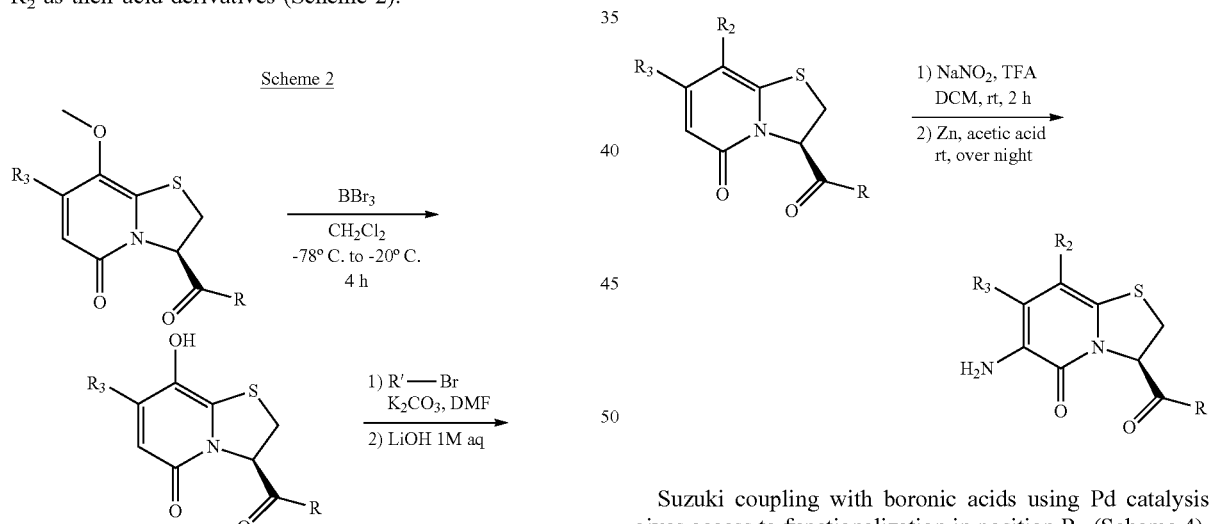

Scheme 3

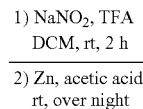

Nitration in the presence of oxygen directly followed by reduction of the nitro compound gives access to amino substituent in $R_4$ (Scheme 3).

Suzuki coupling with boronic acids using Pd catalysis gives access to functionalization in position $R_3$ (Scheme 4).

Scheme 4

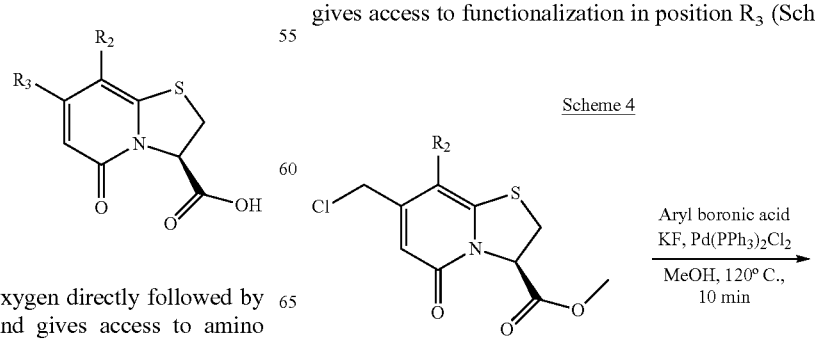

Cleavage of the Cbz protection with HBr/HOAc followed by N-alkylation with alkyl halide or by reductive amination gave the alkyl amines while N-acylation with acyl halides or sufonyl chlorides gave access to carbamates, carboxamides and sulphonamides with different $Z_1$ and/or $Z_2$ substituents (Scheme 5).

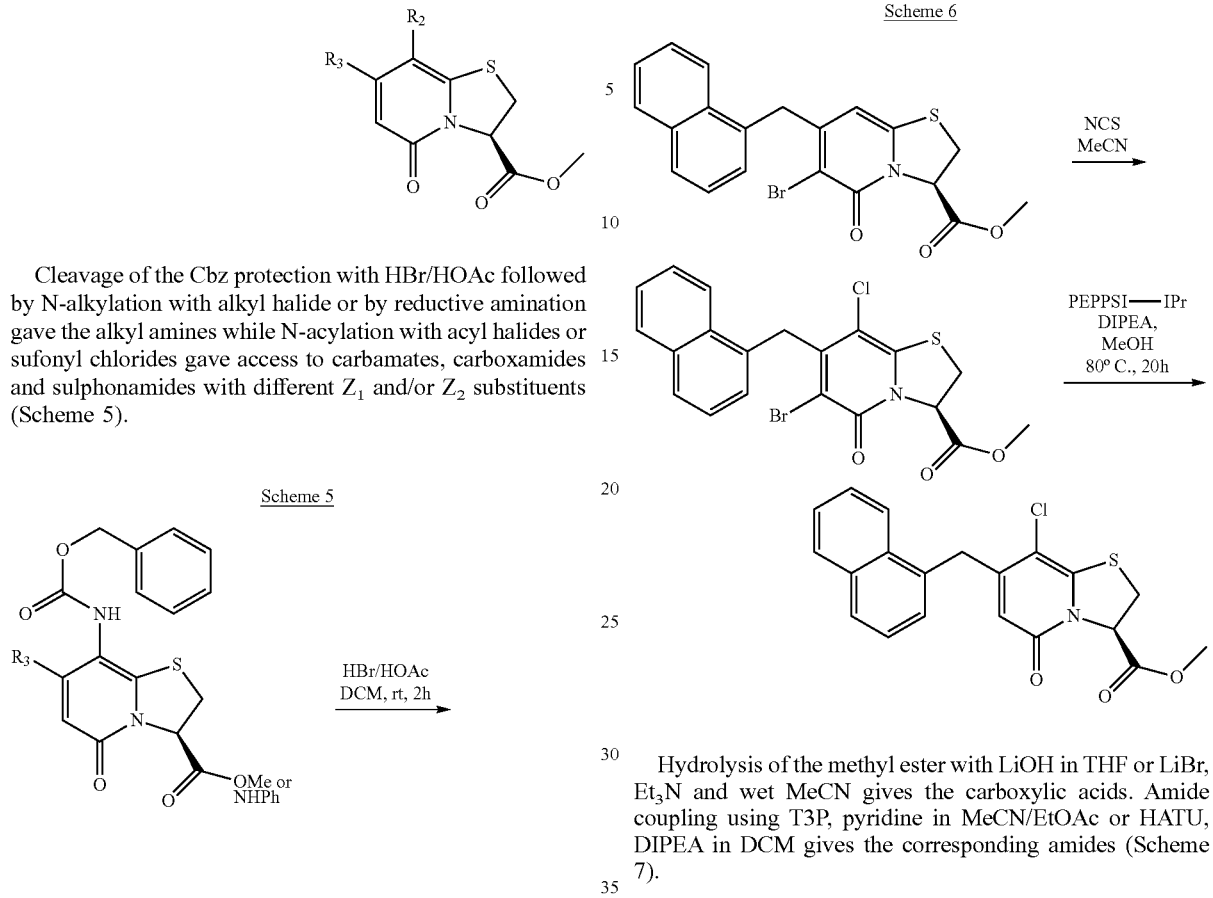

Chlorination with NCS in MeCN directly followed by de-bromination using PEPPSI-IPr™ gave chloro in position $R_2$ (Scheme 6).

Hydrolysis of the methyl ester with LiOH in THF or LiBr, $Et_3N$ and wet MeCN gives the carboxylic acids. Amide coupling using T3P, pyridine in MeCN/EtOAc or HATU, DIPEA in DCM gives the corresponding amides (Scheme 7).

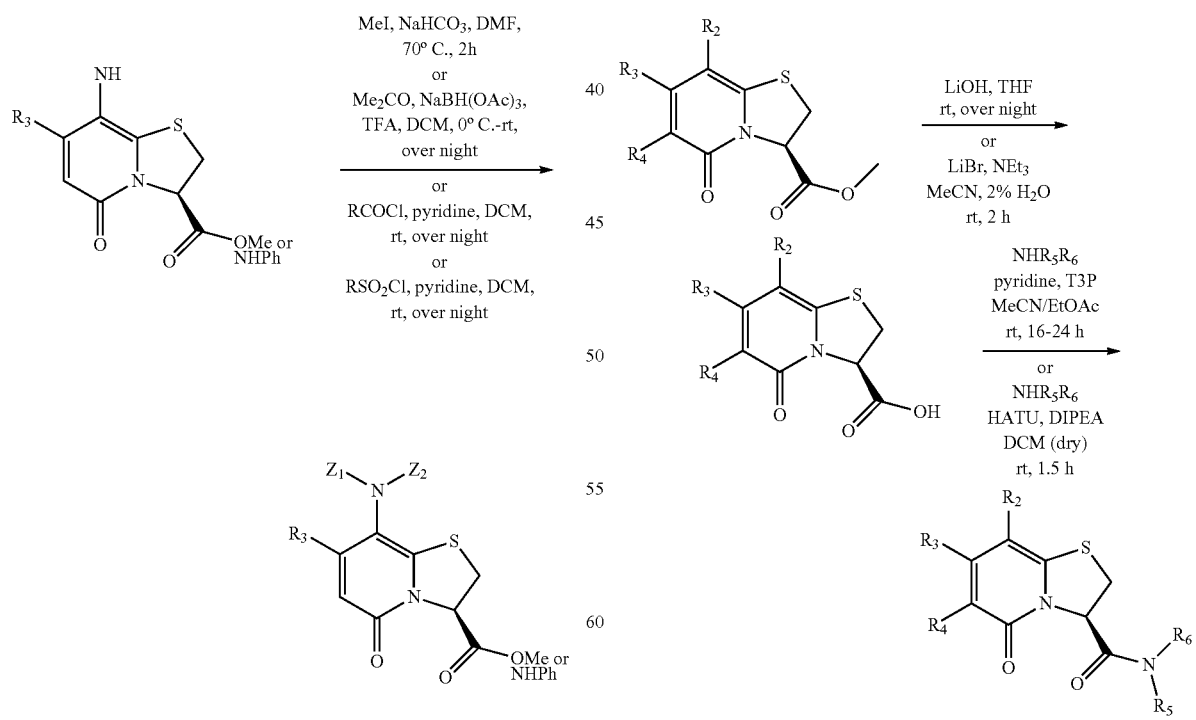

Oxadiazole and triazole were prepared from the carboxylic acids according to Scheme 8.

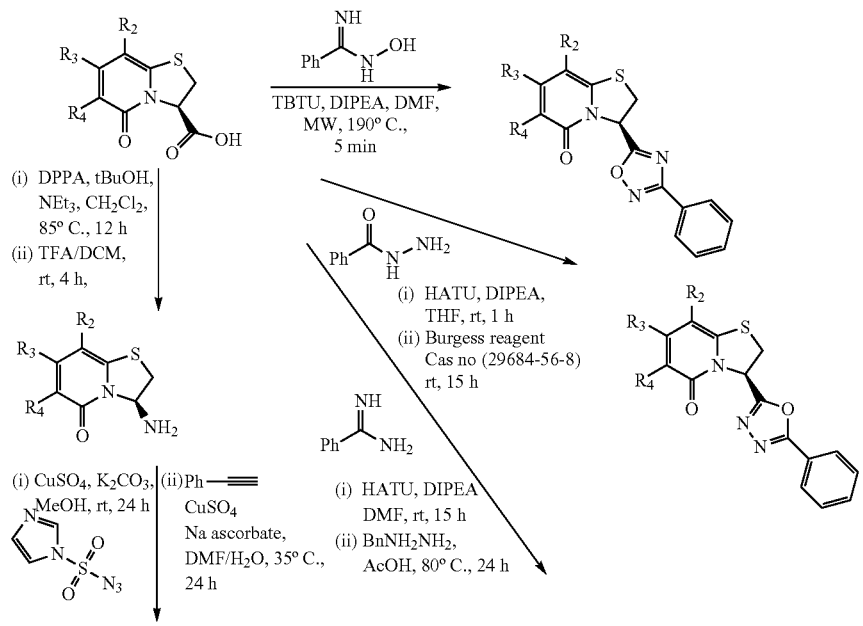
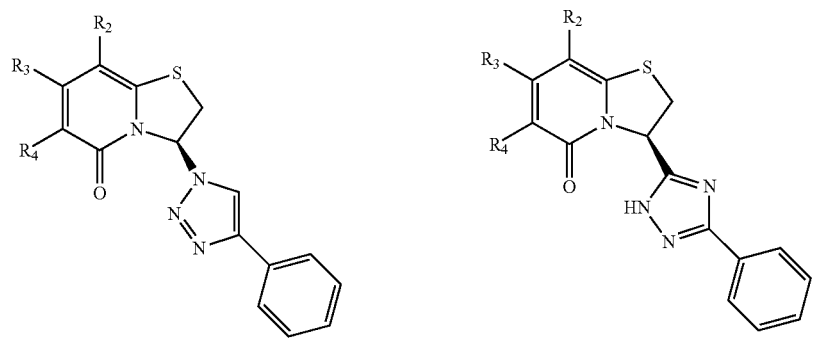
Further, the compounds of the present disclosure may be prepared as in Scheme 9 or Scheme 10.
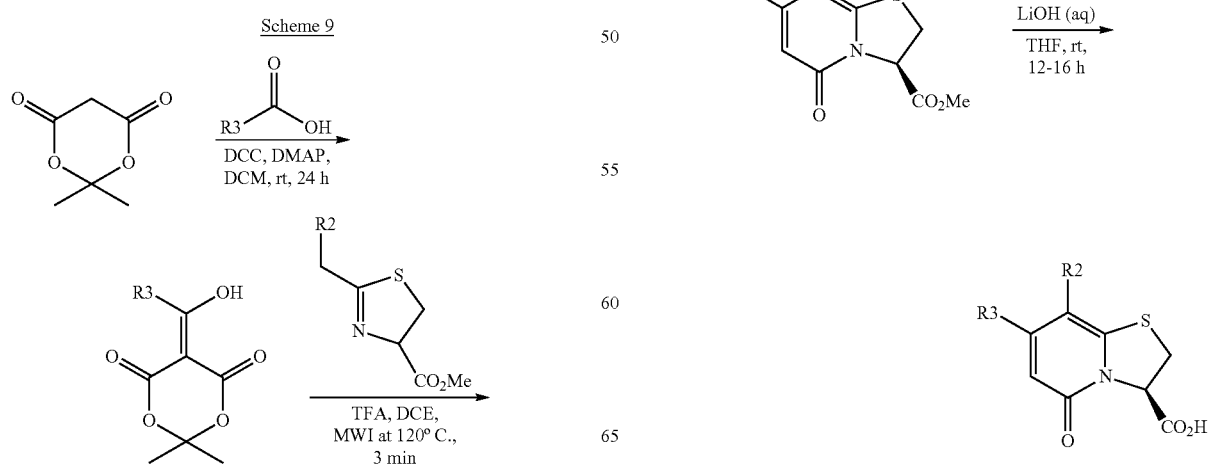

Scheme 10

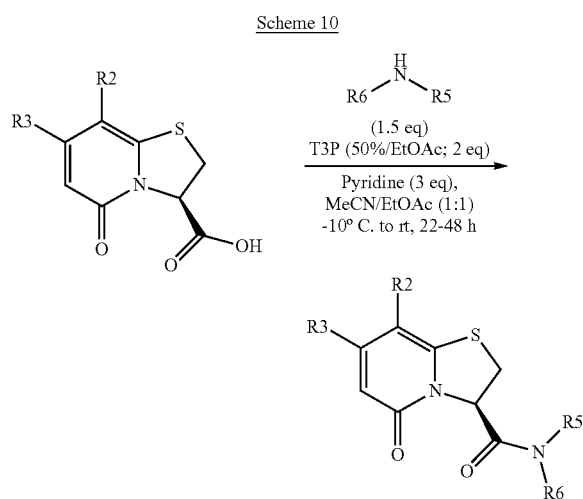

Certain intermediates may be used in the synthesis of compounds of the present disclosure such as compounds of Formula I. The present disclosure is directed to such intermediates and/or use thereof in the manufacture of compounds of the present disclosure such as compounds of Formula I. Examples of such intermediates include the following compounds:

(3R)-7-Hydroxy-6-[(1-naphthyl)methyl]-4-oxo-1-thia-3a-aza-3-indancarboxylic acid;
(3R)-7-Methoxy-4-oxo-6-[(2,3-xylyl)methyl]-1-thia-3a-aza-3-indancarboxylic acid;
(3R)-5-Amino-7-methoxy-4-oxo-6-[(2,3-xylyl)methyl]-1-thia-3a-aza-3-indancarboxylic acid;
(3R)-7-(Methoxycarbonylamino)-6-[(1-naphthyl)methyl]-4-oxo-1-thia-3a-aza-3-indancarboxylic acid;
(3R)-7-Acetylamino-6-[(1-naphthyl)methyl]-4-oxo-1-thia-3a-aza-3-indancarboxylic acid;
(3R)-7-(Methylsulfonylamino)-6-[(1-naphthyl)methyl]-4-oxo-1-thia-3a-aza-3-indancarboxylic acid; and
(3R)-7-(Dimethylamino)-6-[(1-naphthyl)methyl]-4-oxo-1-thia-3a-aza-3-indancarboxylic acid.

Further examples of such intermediates include the following compounds:

Methyl (3R)-7-methoxy-6-[(1-naphthyl)methyl]-4-oxo-1-thia-3a-aza-3-indancarboxylate;
Methyl (3R)-6-(chloromethyl)-7-methoxy-4-oxo-1-thia-3a-aza-3-indancarboxylate;
Methyl (3R)-7-methoxy-4-oxo-6-[(2,3-xylyl)methyl]-1-thia-3a-aza-3-indancarboxylate;
Methyl (3R)-7-hydroxy-6-[(1-naphthyl)methyl]-4-oxo-1-thia-3a-aza-3-indancarboxylate; and
Methyl (3R)-6-[(1-naphthyl)methyl]-4-oxo-7-(trifluoromethyl)-1-thia-3a-aza-3-indancarboxylate.

In this document, unless otherwise stated, the naming and the drawing of the chemical compounds and radicals have been made using the program Chem Doodle version 7.0.1 or version 7.0.2. If the name and drawing are inconsistent, the chemical structure shall be considered to be correct.

The previously mentioned compound 7-(naphthalen-1-ylmethyl)-8-cyclopropyl-5-oxo-N-phenyl-5H-[1,3]thiazolo[3,2-a]pyridine-3-carboxamide (KSK 120) corresponds to the Chem Doodle name 9-Anilinocarbonyl-5-cyclopropyl-4-[(1-naphthyl)methyl]-7-thia-1-azabicyclo[4.3.0]nona-3,5,8-trien-2-one.

The disclosure is further illustrated by the following non-limitative Examples.

EXAMPLES

Abbreviations

ATCC American Type Culture Collection
Bn bensyl
Cbz Carboxybenzyl
DAPI 4',6-diamidino-2-phenylindole
DCC dicyclocarboimide
DCE 1,2-dichloroethane
DCM dichloromethane
DIPEA diisopropylethylamine
DMAP N,N-dimethylaminopyridine
DMF dimethylformamide
DPPA diphenylphosphoryl azide
DMSO dimethyl sulphoxide
EBs Chlamydia trachomatis elementary bodies
ESI-TOFI Electro Spray Ionization—Time of Flight Isochronous
FITC Fluorescein isothiocyanate
HATU 1-[Bis(dimethylamino)methylene]-1H-1,2,3-triazolo[4,5b]pyridinium 3-oxid hexafluorophosphate
HEPES 4-(2-hydroxyethyl)-1-piperazineethanesulfonic acid buffering agent
HPLC High Pressure Liquid Chromatography
HRMS High Resolution Mass Spectroscopy
IFU infection forming units
IUPAC International Union of Pure and Applied Chemistry
MOI multiplicity of infection
MW Micro Wave
NMR Nuclear Magnetic Resonance
PEPPSI-IPr [1,3-Bis(2,6-Diisopropylphenyl)imidazol-2-ylidene](3-chloropyridyl)palladium(II) dichloride cas nr 905459-27-0
RPMI Roswell Park Memorial Institute medium
SPG Succinic acid, Sodium phosphate monobasic monohydrate, Glycine buffer
TBTU N,N,N,N'-Tetramethyl-O-(benzotriazol-1-yl)uronium tetrafluoroborate
THF tetrahydrofurane
TFA trifluoroacetic acid
T3P 2,4,6-Tripropyl-1,3,5,2,4,6-trioxatriphosphorinane-2,4,6-trioxide solution Chemistry All reagents and solvents were used as received from commercial suppliers, unless indicated otherwise. Triethylamine, N,N-diisopropylethylamine and pyridine were passed through activated alumina oxide and dried over 3 Å molecular sieves prior to use. $CH_2Cl_2$, THF and DMF were dried in a solvent drying system ($CH_2Cl_2$ and THF drying agent: neutral alumina; DMF drying agent: activated molecular sieves equipped with an isocyanate scrubber) and collected fresh prior to every reaction. NaH was prewashed with pentane and dried under vacuum prior to use. Microwave reactions were performed using a Biotage Initiator microwave synthesizer in sealed vessels with temperature monitoring by an internal IR probe. TLC was performed on aluminum backed silica gel plates (median pore size 60 Å) and detected with UV light at 254 nm. Column chromatography was performed using silica gel with average particle diameter 50 μM (range 40-65 μM, pore diameter 53 Å) and eluents are given in brackets. Preparatory HPLC purifications were performed on a system equipped with a 250×21.5 mm Nucleodur® C18 HTEC (particle size 5 μM) column using a flow rate of 20 mL/min and detection at 220 nm. Optical rotation was measured with a polarimeter at 25° C. at 589 nm. $^1$H and $^{13}$C NMR spectra were recorded on a 400 or 600 MHz spectrometer at 298 K and calibrated by using the residual peak of the solvent as the internal standard (CDCl$_3$: $\delta_H$=7.26 ppm; $\delta_C$=77.16 ppm; DMSO-d$_6$: $\delta_H$=2.50 ppm; $\delta_C$=39.50 ppm). HRMS was performed by using a mass spectrometer with ESI-TOF (ESI+); sodium formate was used as the calibration chemical. Compounds are named according to IUPAC nomenclature by ChemDoodle version 7.0.1 or version 7.0.2.

The following Examples were prepared in accordance or in analogy with any one of Schemes disclosed in this document unless otherwise stated.

Example 1

{(3R)-7-Methoxy-6-[(1-naphthyl)methyl]-4-oxo-1-thia-3a-aza-3-indanyl}anilinoformaldehyde

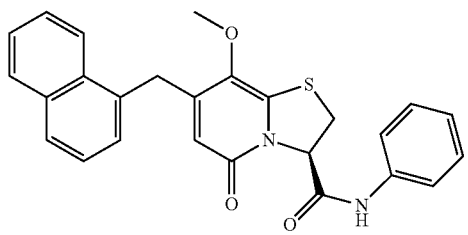 [SMILES: COc1c(Cc2cccc3ccccc23)cc(=O)n2c1SC[C@H]2C(=O)Nc1ccccc1]

$^1$H-NMR, 400 MHz, (CDCl$_3$) δ 3.66 (dd, J=7.9, 11.2 Hz, 1H), 3.76 (s, 3H), 4.19-4.39 (m, 3H), 5.76 (d, J=7.9 Hz, 1H), 5.79 (s, 1H), 7.05-7.10 (m, 1H), 7.25-7.30 (m, 2H), 7.33 (d, J=7.0 Hz, 1H), 7.41-7.54 (m, 5H), 7.78-7.84 (m, 2H), 7.85-7.90 (m, 1H), 10.33 (s, 1H).

Example 2

{(3R)-7-Methoxy-6-[(1-naphthyl)methyl]-4-oxo-1-thia-3a-aza-3-indanyl}(p-toluidino)formaldehyde

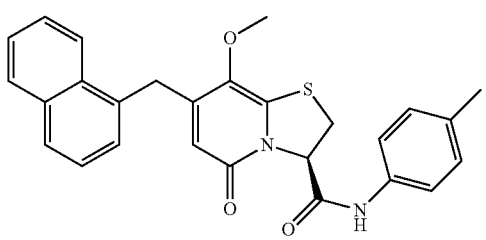 [SMILES: COc1c(Cc2cccc3ccccc23)cc(=O)n2c1SC[C@H]2C(=O)Nc1ccc(C)cc1]

$^1$H-NMR, 400 MHz, (CDCl$_3$) δ 2.28 (s, 3H), 3.62 (dd, J=7.9, 11.2 Hz, 1H), 3.76 (s, 3H), 4.17-4.40 (m, 3H), 5.73 (d, J=7.9 Hz, 1H), 5.78 (s, 1H), 7.03-7.08 (m, 2H), 7.31-7.52 (m, 6H), 7.77-7.91 (m, 3H), 10.23 (s, 1H).

Example 3

{(3R)-7-Methoxy-4-oxo-6-[(2,3-xylyl)methyl]-1-thia-3a-aza-3-indanyl}anilinoformaldehyde

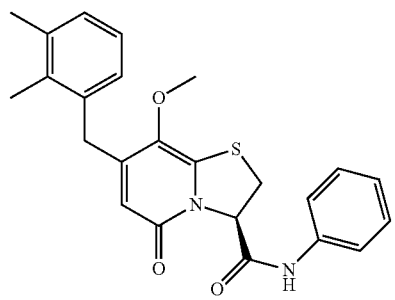 [SMILES: COc1c(Cc2cccc(C)c2C)cc(=O)n2c1SC[C@H]2C(=O)Nc1ccccc1]

$^1$H-NMR, 400 MHz, (CDCl$_3$) δ 2.10 (s, 3H), 2.29 (s, 3H), 3.66 (dd, J=7.9, 11.2 Hz, 1H), 3.72 (s, 3H), 3.86 (dd, J=17.4, 35.7 Hz, 2H), 4.26 (d, J=11.2 Hz, 1H), 5.76-5.81 (m, 2H), 6.93-6.98 (m, 1H), 7.03-7.12 (m, 3H), 7.26-7.32 (m, 2H), 7.52-7.57 (m, 2H), 10.40 (br s, 1H).

Example 4

{(3R)-7-Methoxy-4-oxo-6-[(2,3-xylyl)methyl]-1-thia-3a-aza-3-indanyl}(3-fluoro-5-toluidino)formaldehyde

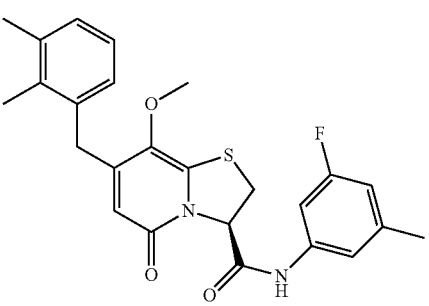

$^1$H-NMR, 400 MHz, (CDCl$_3$) δ 2.10 (s, 3H), 2.27 (s, 3H), 2.29 (s, 3H), 3.65 (dd, J=7.9, 11.3 Hz, 1H), 3.72 (s, 3H), 3.86 (dd, J=17.3, 35.8 Hz, 2H), 4.20 (d, J=11.3 Hz, 1H), 5.76 (dd, J=7.9 Hz, 1H), 5.79-5.77 (m, 1H), 6.57-6.61 (m, 1H), 6.94-6.97 (m, 2H), 7.04-7.10 (m, 2H), 7.31-7.36 (m, 1H), 10.48 (bs, 1H).

Example 5

{(3R)-7-Methoxy-4-oxo-6-[(2,3-xylyl)methyl]-1-thia-3a-aza-3-indanyl}(p-toluidino)formaldehyde

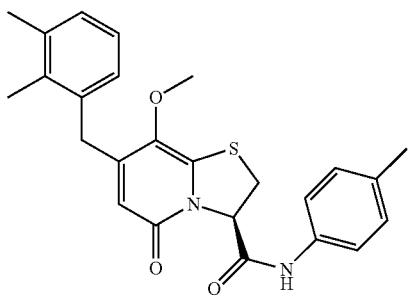

$^1$H-NMR, 400 MHz, (CDCl$_3$) δ 2.10 (s, 3H), 2.29 (s, 3H), 2.30 (s, 3H), 3.64 (dd, J=7.9, 11.1 Hz, 1H), 3.72 (s, 3H), 3.86 (dd, J=17.3, 33.9 Hz, 2H), 4.21 (d, J=11.1 Hz, 1H), 5.72-5.80 (m, 2H), 6.94-6.98 (m, 1H), 7.03-7.11 (m, 4H), 7.39-7.45 (m, 2H), 10.28 (bs, 1H).

Example 6

{(3R)-5-Amino-7-methoxy-6-[(1-naphthyl)methyl]-4-oxo-1-thia-3a-aza-3-indanyl}anilinoformaldehyde

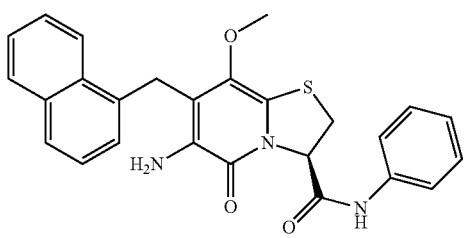 [SMILES: COc1c(Cc2cccc3ccccc23)c(N)c(=O)n2c1SC[C@H]2C(=O)Nc1ccccc1]

$^1$H-NMR, 400 MHz, (CDCl$_3$) δ 3.59 (s, 3H), 2.67 (dd, J=7.7, 11.2 Hz, 1H), 3.99 (bs, 2H), 4.20 (d, J=11.2 Hz, 1H), 4.34 (dd, J=16.5, 29.0 Hz, 2H), 5.85 (d, J=7.7 Hz, 1H), 7.07-7.16 (m, 2H), 7.28-7.39 (m, 3H), 7.53-7.63 (m, 4H), 7.77 (d, J=8.3 Hz, 1H), 7.88-7.92 (m, 1H), 8.17 (d, J=8.3 Hz, 1H), 10.4 (bs, 1H).

Example 7

{(3R)-5-Amino-7-methoxy-4-oxo-6-[(2,3-xylyl)methyl]-1-thia-3a-aza-3-indanyl}(p-toluidino)formaldehyde

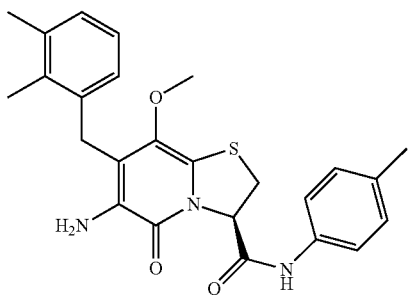

$^1$H-NMR, 400 MHz, (CDCl$_3$) δ 2.29 (s, 3H), 2.30 (s, 3H), 2.32 (s, 3H), 3.57 (s, 3H), 3.66 (dd, J=7.7, 11.2 Hz, 1H), 3.75-4.05 (m, 4H), 4.20 (d, J=11.2 Hz, 1H), 5.84 (d, J=7.7 Hz, 1H), 6.79 (d, J=7.4 Hz, 1H), 6.99 (t, J=7.4 Hz, 1H), 7.06 (d, J=7.4 Hz, 1H), 7.11 (d, J=8.2 Hz, 2H), 7.46 (d, J=8.2 Hz, 2H), 10.29 (br s, 1H).

Example 8

{(3R)-5-Amino-7-methoxy-4-oxo-6-[(2,3-xylyl)methyl]-1-thia-3a-aza-3-indanyl}(3-fluoro-5-toluidino)formaldehyde

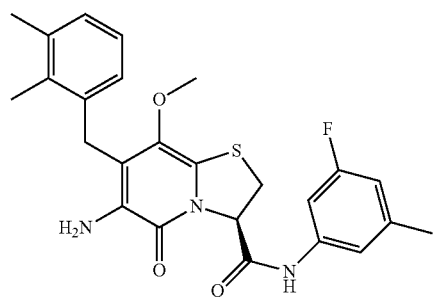

$^1$H-NMR, 400 MHz, (CDCl$_3$) δ 2.29 (s, 3H), 2.30 (s, 3H), 2.32 (s, 3H), 3.57 (s, 3H), 3.66 (dd, J=7.7, 11.3 Hz, 1H), 3.78-3.99 (m, 4H), 4.17 (d, J=11.3 Hz, 1H), 5.82 (d, J=7.7 Hz, 1H), 6.61 (d, J=9.3 Hz, 1H), 6.77-6.81 (m, 1H), 6.95-7.08 (m, 3H), 7.30-7.36 (m, 1H), 10.49 (br s, 1H).

Example 9

{(3R)-5-Amino-7-methoxy-6-[(1-naphthyl)methyl]-4-oxo-1-thia-3a-aza-3-indanyl}(p-toluidino)formaldehyde

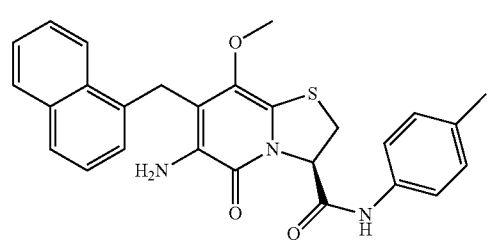 [SMILES: COc1c(Cc2cccc3ccccc23)c(N)c(=O)n2c1SC[C@H]2C(=O)Nc1ccc(C)cc1]

$^1$H-NMR, 400 MHz, (CDCl$_3$) δ 2.31 (s, 3H), 3.58 (s, 3H), 3.67 (dd, J=7.7, 11.2 Hz, 1H), 3.98 (br s, 2H), 4.20 (d, J=11.2 Hz, 1H), 4.34 (dd, J=16.5, 29.1 Hz, 2H), 5.84 (d, J=7.7 Hz, 1H), 7.09.7.16 (m, 3H), 7.33-7.39 (m, 1H), 7.45-7.50 (m, 2H), 7.52-7.62 (m, 2H), 7.77 (d, J=8.2 Hz, 1H), 7.90 (d, J=7.9 Hz, 1H), 8.17 (d, J=8.3 Hz, 1H), 10.29 (br s, 1H).

Example 10

{(3R)-7-Hydroxy-6-[(1-naphthyl)methyl]-4-oxo-1-thia-3a-aza-3-indanyl}anilinoformaldehyde

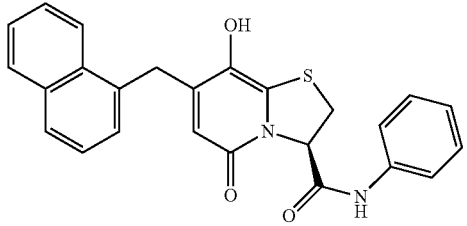 [SMILES: O=C(Nc1ccccc1)[C@@H]1CSc2c(O)c(Cc3cccc4ccccc34)cc(=O)n21]

$^1$H-NMR, 400 MHz, (DMSO) δ 3.57 (dd, J 1.9, 12.0 Hz, 1H), 3.9 (dd, J=8.9, 12.0 Hz, 1H), 4.27 (dd, J=16.8, 34.3 Hz, 2H), 5.27 (s, 1H), 5.48 (dd, J=1.9, 8.9 Hz, 1H), 7.03-7.08 (m, 1H), 7.27-7.33 (m, 2H), 7.42 (d, J=6.9 Hz, 1H), 7.48-7.57 (m, 5H), 7.85-7.99 (m, 3H), 8.60 (s br, 1H), 10.39 (s, 1H).

Example 11

{(3R)-7-Chloro-6-[(1-naphthyl)methyl]-4-oxo-1-thia-3a-aza-3-indanyl}anilinoformaldehyde

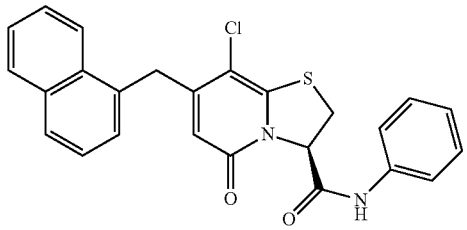 [SMILES: O=C(Nc1ccccc1)[C@@H]1CSc2c(Cl)c(Cc3cccc4ccccc34)cc(=O)n21]

$^1$H-NMR, 400 MHz, (CDCl$_3$) δ 3.70 (dd, J=8.0, 11.3 Hz, 1H), 4.20-4.39 (m, 3H), 5.75 (s, 1H), 5.81 (d, J=8.0 Hz, 1H), 7.04-7.10 (m, 1H), 7.23-7.33 (m, 3H), 7.42-7.53 (m, 5H), 7.67-7.75 (m, 1H), 7.80-7.92 (m, 2H), 10.01 (s, 1H).

Example 12

{(3R)-6-[(1-Naphthyl)methyl]-4-oxo-7-(trifluoromethyl)-1-thia-3a-aza-3-indanyl}anilinoformaldehyde

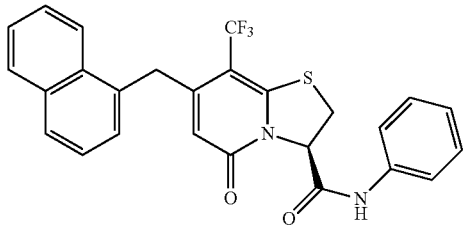 [SMILES: O=C(Nc1ccccc1)[C@@H]1CSc2c(C(F)(F)F)c(Cc3cccc4ccccc34)cc(=O)n21]

$^1$H-NMR, 400 MHz, (DMSO-d$_6$) δ 3.66 (dd, J=1.4, 12.0 Hz, 1H), 3.99 (dd, J=9.4, 12.0 Hz, 1H), 4.40 (s, 2H), 5.40 (s, 1H), 5.59 (d, J=9.4 Hz, 1H), 7.05-7.10 (m, 1H), 7.28-7.34 (m, 2H), 7.40-7.43 (m, 1H), 7.50-7.59 (m, 5H), 7.76-7.81 (m, 1H), 7.89-7.94 (m, 1H), 7.96-8.01 (m, 1H), 10.51 (bs, 1H).

Example 13

{(3R)-5-Amino-7-methoxy-4-oxo-6-[(2,3-xylyl)methyl]-1-thia-3a-aza-3-indanyl}anilinoformaldehyde

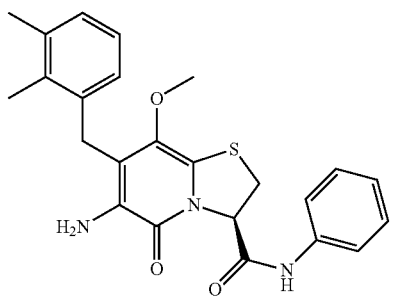 [SMILES: COc1c(Cc2cccc(C)c2C)c(N)c(=O)n2c1SC[C@H]2C(=O)Nc1ccccc1]

$^1$H-NMR, 400 MHz, (CDCl$_3$) δ 2.29 (s, 3H), 2.33 (s, 3H), 3.57 (s, 3H), 3.66 (dd, J=7.7, 11.2 Hz, 1H), 3.78-4.01 (m, 4H), 4.19 (d, J=11.2 Hz, 1H), 5.85 (d, J=7.7 Hz, 1H), 6.80 (d, J=7.5 Hz, 1H), 6.96-7.13 (m, 3H), 7.27-7.34 (m, 2H), 7.55-7.61 (m, 2H), 10.41 (bs, 1H).

Example 14

(3R)-5-Amino-7-methoxy-3-(3-phenyl-1,2,4-oxadiazol-5-yl)-6-[(2,3-xylyl)methyl]-1-thia-3a-aza-4-indanone

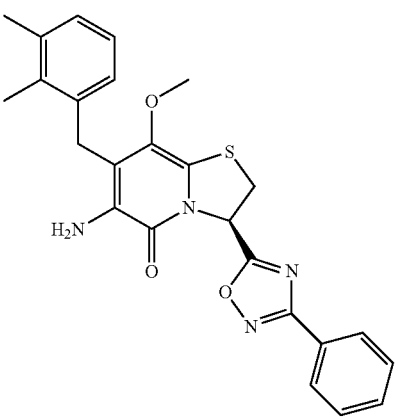 [SMILES: COc1c(Cc2cccc(C)c2C)c(N)c(=O)n2c1SC[C@H]2c1nc(-c2ccccc2)no1]

$^1$H-NMR, 400 MHz, (CDCl$_3$) δ 2.30 (s, 3H), 2.33 (s, 3H), 3.59 (s, 3H), 3.73 (dd, J=1.8, 11.8 Hz, 1H), 3.81-4.03 (m, 5H), 6.47 (dd, J=1.8, 7.5 Hz, 1H), 6.86 (d, J=7.5, 1H), 6.98-7.09 (m, 2H), 7.43-7.53 (m, 3H), 8.04-8.09 (m, 2H).

Example 15

(3R)-7-Methoxy-3-(5-phenyl-1,3,4-oxadiazol-2-yl)-6-[(2,3-xylyl)methyl]-1-thia-3a-aza-4-indanone

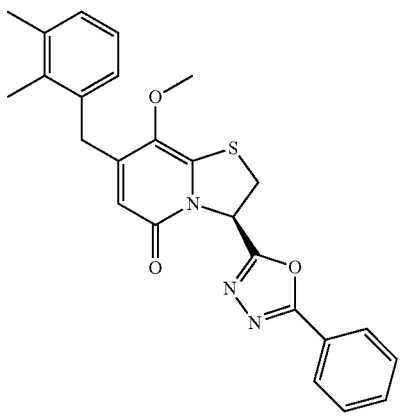 [SMILES: COc1c(Cc2cccc(C)c2C)cc(=O)n2c1SC[C@H]2c1nnc(-c2ccccc2)o1]

¹H-NMR, 400 MHz, (DMSO-d₆) δ 2.09 (s, 3H), 2.26 (s, 3H), 3.70 (s, 3H), 3.84-3.89 (m, 3H), 4.09 (dd, J=8.2, 11.9 Hz, 1H), 5.39-5.40 (m, 1H), 6.42 (dd, J=1.9, 8.2 Hz, 1H), 6.99-7.12 (m, 3H), 7.58-7.68 (m, 3H), 7.93-7.99 (m, 2H).

Example 16

(3R)-7-Methoxy-3-(3-phenyl-1,2,4-oxadiazol-5-yl)-6-[(2,3-xylyl)methyl]-1-thia-3a-aza-4-indanone

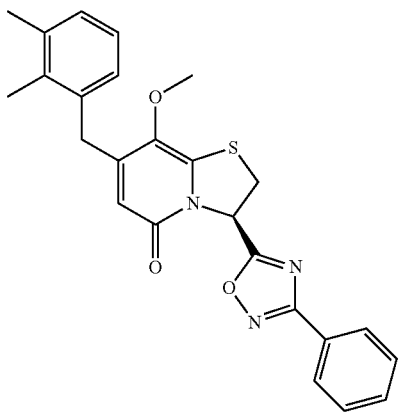 [SMILES: COc1c(Cc2cccc(C)c2C)cc(=O)n2c1SC[C@H]2c1nc(-c2ccccc2)no1]

¹H-NMR, 400 MHz, (CDCl₃) δ 2.13 (s, 3H), 2.30 (s, 3H), 3.72-3.76 (m, 4H), 3.89 (dd, J=17.2, 20.3 Hz, 2H), 3.97 (dd, J=7.8, 11.8 Hz, 1H), 5.75 (t, J=1.1 Hz, 1H), 6.40 (dd, J=1.7, 7.8 Hz, 1H), 6.97-7.11 (m, 3H), 7.43-7.53 (m, 3H), 8.02-8.06 (m, 2H).

Example 17

{(3R)-7-Methoxy-4-oxo-6-[(2,3-xylyloxy)methyl]-1-thia-3a-aza-3-indanyl}(5-chloro-2-pyridylamino)formaldehyde

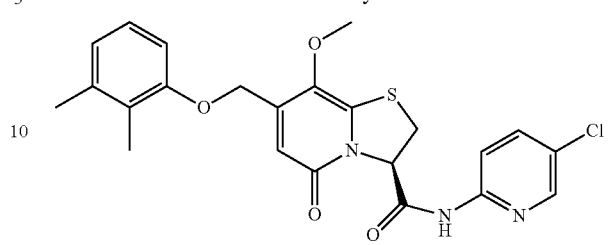

¹H NMR (400 MHz, CDCl₃) δ=2.22 (s, 3H), 2.29 (s, 3H), 3.71 (dd, J=7.6, 11.2 Hz, 1H), 3.76 (s, 3H), 4.20 (d, J=11.2 Hz, 1H), 4.91-5.00 (m, 2H), 5.88 (d, J=7.6 Hz, 1H), 6.68 (s, 1H), 6.71 (d, J=8.0 Hz, 1H), 6.82 (d, J=7.6 Hz, 1H), 7.04 (dd, J=7.6, 8.0 Hz, 1H), 7.63 (dd, J=2.4, 8.8 Hz, 1H), 8.10 (d, J=8.8 Hz, 1H), 8.25 (d, J=2.4 Hz, 1H), 10.82 (s, 1H).

Example 18

{(3R)-7-Methoxy-4-oxo-6-[(2,3-xylyloxy)methyl]-1-thia-3a-aza-3-indanyl}(5-chloro-2-pyridylamino)formaldehyde

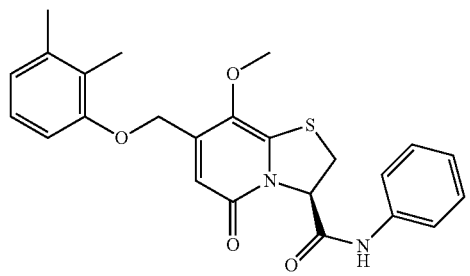 [SMILES: COc1c(COc2cccc(C)c2C)cc(=O)n2c1SC[C@H]2C(=O)Nc1ccccc1]

¹H NMR (400 MHz, CDCl₃) δ=2.23 (s, 3H), 2.30 (s, 3H), 3.68 (dd, J=7.6, 11.2 Hz, 1H), 3.76 (s, 3H), 4.29 (d, J=11.2 Hz, 1H), 4.92-5.01 (m, 2H), 5.85 (d, J=7.6 Hz, 1H), 6.62 (s, 1H), 6.72 (d, J=8.0 Hz, 1H), 6.83 (d, J=7.6 Hz, 1H), 7.05 (dd, J=7.6, 8.0 Hz, 1H), 7.10 (d, J=7.6 Hz, 1H), 7.30 (dd, J=7.6, 8.4 Hz, 2H), 7.57 (d, J=8.4 Hz, 2H), 10.37 (s, 1H).

Example 19

Anilino{7-cyclopropyl-4-oxo-6-[(2,3-xylylyloxy)methyl]-1-thia-3a-aza-3-indanyl}formaldehyde

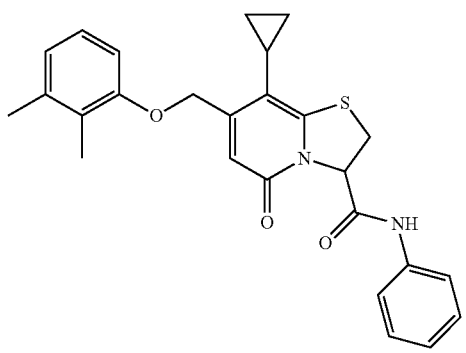 [SMILES: Cc1cccc(OCc2cc(=O)n3c(c2C2CC2)SCC3C(=O)Nc2ccccc2)c1C]

¹H NMR (400 MHz, CDCl₃) δ=0.55-0.63 (m, 1H), 0.68-0.78 (m, 1H), 0.85-1.03 (m, 2H), 1.60-1.68 (m, 1H), 2.24 (s, 3H), 2.30 (s, 3H), 3.59 (dd, J=8.0, 11.2 Hz, 1H), 4.20 (d, J=11.2 Hz, 1H), 5.06-5.09 (m, 2H), 5.86 (d, J=7.9 Hz, 1H), 6.66-6.70 (m, 2H), 6.83 (d, J=7.6 Hz, 1H), 7.02-7.10 (m, 2H), 7.25-7.32 (m, 2H), 7.53-7.58 (m, 2H), 10.31 (br s, 1H).

Example 20

{(3R)-7-Cyclopropyl-4-oxo-6-[(2,3-xylyl)methyl]-1-thia-3a-aza-3-indanyl}(p-toluidino)formaldehyde

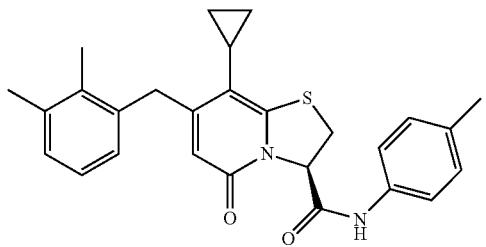

¹H NMR (400 MHz, CDCl₃) δ=0.57-0.66 (m, 1H), 0.71-0.80 (m, 1H), 0.85-0.95 (m, 1H), 0.97-1.01 (m, 1H), 1.58-1.68 (m, 1H), 2.07 (s, 3H), 2.28 (s, 3H), 2.30 (s, 3H), 3.55 (dd, J=8.0, 11.2 Hz, 1H), 3.92-4.04 (m, 2H), 4.17 (d, J=11.2 Hz, 1H), 5.76-5.80 (m, 2H), 6.89-6.92 (m, 1H), 7.03-7.11 (m, 4H), 7.39-7.44 (m, 2H), 10.23 (s, 1H).

Example 21

{(3R)-6-[(p-Chlorophenyl)methyl]-7-cyclopropyl-4-oxo-1-thia-3a-aza-3-indanyl}(p-toluidino)formaldehyde

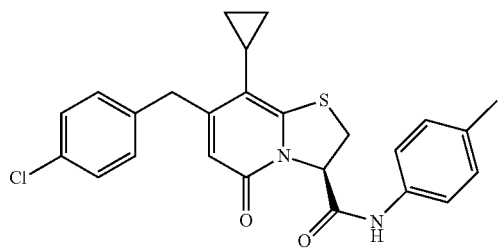 [SMILES: Cc1ccc(NC(=O)[C@@H]2CSc3c(C4CC4)c(Cc4ccc(Cl)cc4)cc(=O)n32)cc1]

¹H NMR (400 MHz, CDCl₃) δ=0.52-0.61 (m, 1H), 0.65-0.74 (m, 1H), 0.79-0.89 (m, 1H), 0.91-1.01 (m, 1H), 1.36-1.45 (m, 1H), 2.29 (s, 3H), 3.55 (dd, J=8.0, 11.2 Hz, 1H), 3.90 (d, J=16.0 Hz, 1H), 4.00 (d, J=16.0 Hz, 1H), 4.16 (d, J=11.2 Hz, 1H), 5.81 (d, 7.9, 1H), 6.05 (s, 1H), 7.06-7.12 (m, 4H), 7.25-7.30 (m, 2H), 7.40-7.45 (m, 2H), 10.20 (s, 1H).

Example 22

(3R)-7-Cyclopropyl-6-[(1-naphthyl)methyl]-3-(5-phenyl-2H-1,2,4-triazol-3-yl)-1-thia-3a-aza-4-indanone

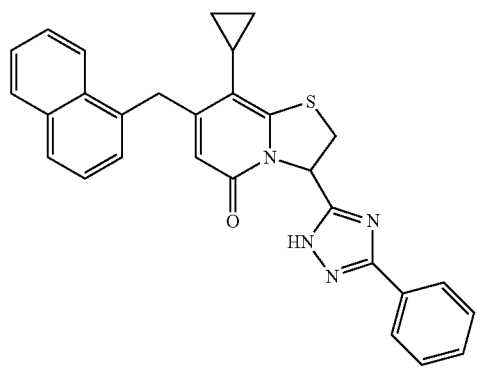 [SMILES: O=c1cc(Cc2cccc3ccccc23)c(C2CC2)c2n1C(c1nc(-c3ccccc3)n[nH]1)CS2]

¹H NMR (400 MHz, DMSO-d₆) δ=0.62-0.71 (m, 1H), 0.74-0.82 (m, 1H), 0-84-0.99 (m, 2H), 1-70-1.79 (m, 1H), 3.50 (dd, J=0.9, 11.6 Hz, 1H), 3.96 (dd, J=8.1, 11.6 Hz, 1H), 4.39-4.55 (m, 2H), 5.30 (s, 1H), 6.14 (dd, J=0.9, 8.0 Hz, 1H), 7.41 (d, J=6.5 Hz, 1H), 7.44-7.59 (m, 6H), 7.85-8.00 (m, 5H), 14.21 (br s, 1H).

Example 23

Anilino{7-(isopropylamino)-6-[(1-naphthyl)methyl]-4-oxo-1-thia-3a-aza-3-indanyl}formaldehyde

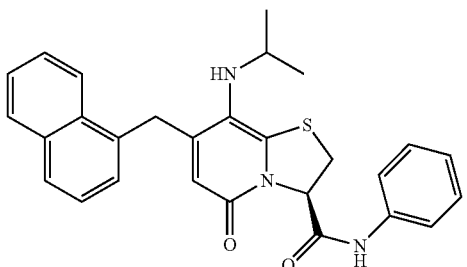

¹H NMR (400 MHz, DMSO-d₆) δ 10.36 (s, 1H), 8.03-7.92 (m, 1H), 7.90-7.76 (m, 2H), 7.63-7.47 (m, 5H), 7.43 (dd, J=7.1, 1.3 Hz, 1H), 7.30 (dd, J=8.5, 7.3 Hz, 2H), 7.15-6.99 (m, 1H), 5.48 (dd, J=9.0, 2.1 Hz, 1H), 5.16 (s, 1H), 4.42 (d, J=17.1 Hz, 1H), 4.29 (d, J=17.1 Hz, 1H), 3.87 (dd, J=11.9, 9.0 Hz, 1H), 3.65-3-60 (m, 1H), 3.50 (dd, J=11.9, 2.1 Hz, 1H), 1.22-1.02 (m, 6H).

Example 24

{(3R)-7-(Dimethylamino)-6-[(1-naphthyl)methyl]-4-oxo-1-thia-3a-aza-3-indanyl}anilinoformaldehyde

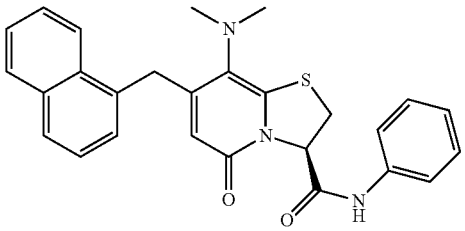 [SMILES: CN(C)c1c(Cc2cccc3ccccc23)cc(=O)n2c1SC[C@H]2C(=O)Nc1ccccc1]

$^1$H NMR (400 MHz, DMSO-d$_6$) δ 10.39 (s, 1H), 7.98-7.94 (m, 1H), 7.93-7.89 (m, 1H), 7.86 (d, J=8.2 Hz, 1H), 7.60-7.46 (m, 5H), 7.40 (d, J=7.1 Hz, 1H), 7.37-7.23 (m, 2H), 7.09-7.02 (m, 1H), 5.45 (dd, J=9.2, 2.4 Hz, 1H), 5.30 (s, 1H), 4.35 (d, J=16.7 Hz, 1H), 4.30 (d, J=16.8 Hz, 1H), 3.92 (dd, J=11.9, 9.2 Hz, 1H), 3.55 (dd, J=12.0, 2.4 Hz, 1H), 2.71 (s, 6H).

Example 25

Anilino{7-(methylsulfonylamino)-6-[(1-naphthyl)methyl]-4-oxo-1-thia-3a-aza-3-indanyl}formaldehyde

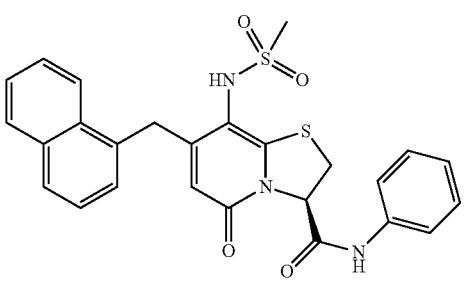 [SMILES: CS(=O)(=O)Nc1c(Cc2cccc3ccccc23)cc(=O)n2c1SC[C@H]2C(=O)Nc1ccccc1]

$^1$H NMR (400 MHz, DMSO-d$_6$) δ 10.41 (s, 1H), 9.29 (s, br, 1H), 8.01-7.94 (m, 1H), 7.93-7.84 (m, 2H), 7.56-7.47 (m, 5H), 7.43 (d, J=7.1 Hz, 1H), 7.35-7.24 (m, 2H), 7.14-6.85 (m, 1H), 5.50 (dd, J=9.1, 2.1 Hz, 1H), 5.03 (s, 1H), 4.47 (d, J=17.7 Hz, 1H), 4.31 (d, J=17.6 Hz, 1H), 4.02 (dd, J=11.9, 9.2 Hz, 1H), 3.60 (dd, J=11.9, 2.1 Hz, 1H), 3.21 (s, 3H).

Example 26

1-{3-Anilinocarbonyl-6-[(1-naphthyl)methyl]-4-oxo-1-thia-3a-aza-7-indanylamino}-1-ethanone

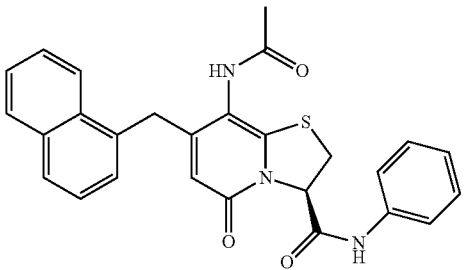 [SMILES: CC(=O)Nc1c(Cc2cccc3ccccc23)cc(=O)n2c1SC[C@H]2C(=O)Nc1ccccc1]

$^1$H NMR (400 MHz, DMSO-d$_6$) δ 10.18 (s, 1H), 9.18 (s, 1H), 8.00-7.71 (m, 3H), 7.58-7.45 (m, 5H), 7.38 (d, J=7.0 Hz, 1H), 7.35-7.23 (m, 2H), 7.12-6.96 (m, 1H), 5.54 (dd, J=9.1, 2.8 Hz, 1H), 5.25 (s, 1H), 4.16 (d, J=17.2 Hz, 1H), 4.11 (d, J=17.2 Hz, 1H), 3.90 (dd, J=11.9, 9.0 Hz, 1H), 3.56 (dd, J=11.8, 2.8 Hz, 1H), 2.01 (s, 3H).

Example 27

{(3R)-7-(Methoxycarbonylamino)-6-[(1-naphthyl)methyl]-4-oxo-1-thia-3a-aza-3-indanyl}anilinoformaldehyde

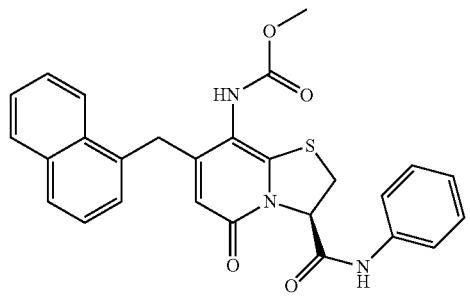 [SMILES: COC(=O)Nc1c(Cc2cccc3ccccc23)cc(=O)n2c1SC[C@H]2C(=O)Nc1ccccc1]

$^1$H NMR (400 MHz, DMSO-d$_6$) δ 10.41 (s, 1H), 8.90 (s, 1H), 8.02-7.95 (m, 1H), 8.19-7.77 (m, 1H), 7.86 (d, J=7.7 Hz, 1H), 7.53 (dt, J=10.4, 7.8 Hz, 5H), 7.42 (d, J=7.2 Hz, 1H), 7.31 (t, J=7.8 Hz, 2H), 7.07 (t, J=7.4 Hz, 1H), 5.51 (dd, J=9.2, 2.3 Hz, 1H), 5.15 (s, 1H), 4.18 (d, J=17.2 Hz, 1H), 4.12 (d, J=17.0 Hz, 1H), 3.96 (dd, J=11.8, 9.2 Hz, 1H), 3.65 (s, 3H), 3.57 (dd, J=12.0, 2.4 Hz, 1H).

Example 28

(3R)-7-(Cyclopropylmethoxy)-6-[(1-naphthyl)methyl]-4-oxo-1-thia-3a-aza-3-indancarboxylic acid

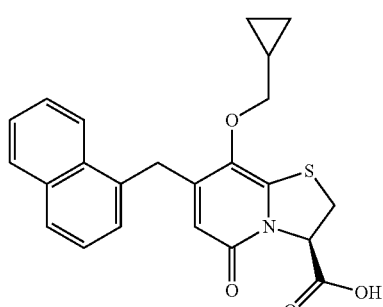

$^1$H-NMR, 400 MHz, (DMSO) δ 0.24-0.30 (m, 2H), 0.51-0.57 (m, 2H), 1.11-1.24 (m, 1H), 3.57 (dd, J=1.7, 11.9 Hz, 1H), 3.71 (dABq, J=7.2, 14.5 Hz, 2H), 3.87 (dd, J=8.9, 11.9 Hz, 1H), 4.31 (dd, J=16.6, 28.4 Hz, 2H), 5.31-5.35 (m, 2H), 7.41-7.45 (m, 1H), 7.47-7.57 (m, 3H), 7.85-7.99 (m, 3H).

Example 29

(3R)-6-[(1-Naphthyl)methyl]-4-oxo-7-(trifluoromethyl)-1-thia-3a-aza-3-indancarboxylic acid

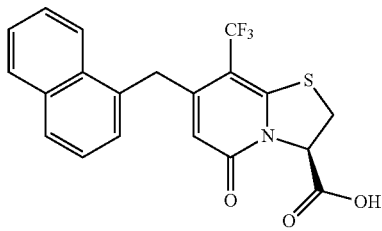 [SMILES: O=C(O)[C@@H]1CSc2c(C(F)(F)F)c(Cc3cccc4ccccc34)cc(=O)n21]

$^1$H-NMR, 400 MHz, (DMSO) δ 3.62 (dd, J=1.2, 11.9 Hz, 1H), 3.88 (dd, J=9.2, 11.9 Hz, 1H), 4.38 (s, 2H), 5.40 (s, 1H), 5.46 (d, J=9.2 Hz, 1H), 7.39-7.42 (m, 1H), 7.49-7.58 (m, 3H), 7.74-7.80 (m, 1H), 7.89-7.94 (m, 1H), 7.96-8.01 (m, 1H).

Example 30

(3R)-7-Isobutoxy-6-[(1-naphthyl)methyl]-4-oxo-1-thia-3a-aza-3-indancarboxylic acid

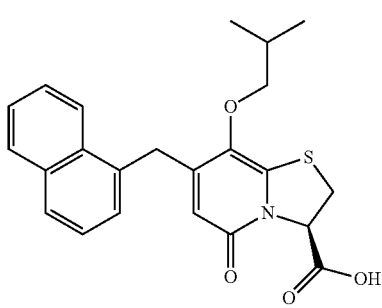 [SMILES: CC(C)COc1c(Cc2cccc3ccccc23)cc(=O)n2c1SC[C@H]2C(=O)O]

$^1$H-NMR, 400 MHz, (DMSO) δ 0.92-0.96 (m, 6H), 1.88-1.99 (m, 1H), 3.52-3.61 (m, 2H), 3.68 (dd, J=6.4, 8.6 Hz, 1H), 3.87 (dd, J=8.9, 11.9 Hz, 1H), 4.29 (dd, J=16.9, 23.5 Hz, 2H), 5.33 (dd, J=1.5, 8.9 Hz, 1H), 5.36 (s, 1H), 7.41-7.44 (m, 1H), 7.48-7.57 (m, 3H), 7.86-7.98 (m, 3H).

Example 31

(3R)-7-(Dimethylamino)-4-oxo-6-[(2,3-xylyl)methyl]-1-thia-3a-aza-3-indancarboxylic acid

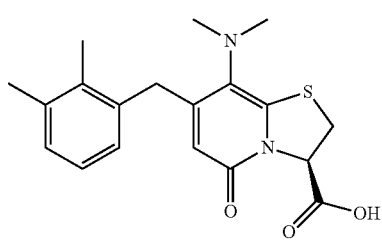 [SMILES: Cc1cccc(Cc2cc(=O)n3c(c2N(C)C)SC[C@H]3C(=O)O)c1C]

$^1$H-NMR, 400 MHz, (DMSO) δ 2.06 (s, 3H), 2.26 (s, 3H), 2.65 (s, 6H), 3.51 (dd, J=1.9, 11.9 Hz, 1H), 3.79-3.89 (m, 3H), 5.28 (s, 1H), 5.33 (dd, J=1.9, 9.1 Hz, 1H), 6.95-7.00 (m, 1H), 7.02-7.10 (m, 2H).

Example 32

(3R)-7-(Dimethylamino)-6-[(4-methyl-1-naphthyl)methyl]-4-oxo-1-thia-3a-aza-3-indancarboxylic acid

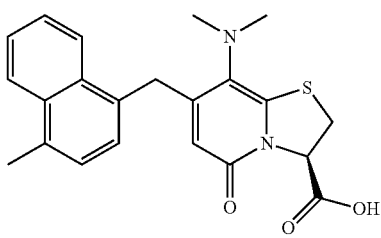 [SMILES: Cc1ccc(Cc2cc(=O)n3c(c2N(C)C)SC[C@H]3C(=O)O)c2ccccc12]

$^1$H-NMR, 400 MHz, (DMSO) δ 2.65 (s, 3H), 2.71 (s, 6H), 3.52 (dd, J=1.9, 11.9 Hz, 1H), 3.84 (dd, J=9.2, 11.9 Hz, 1H), 4.27 (dd, J=16.9, 24.5 Hz, 2H), 5.26 (s, 1H), 5.31 (dd, J=1.9, 9.2 Hz, 1H), 7.26-7.29 (m, 1H), 7.33-7.36 (m, 1H), 7.51-7.59 (m, 2H), 7.84-7.90 (m, 1H), 8.03-8.08 (m, 1H).

Example 33

(3R)-7-(Isopropylamino)-6-[(1-naphthyl)methyl]-4-oxo-1-thia-3a-aza-3-indancarboxylic acid

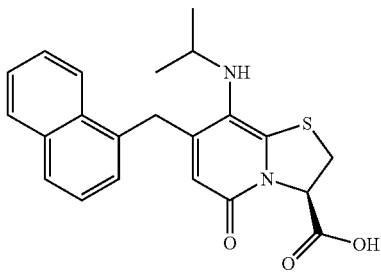 [SMILES: CC(C)Nc1c(Cc2cccc3ccccc23)cc(=O)n2c1SC[C@H]2C(=O)O]

$^1$H NMR (400 MHz, Methanol-$d_4$) δ 7.97-7.91 (m, 1H), 7.88 (d, J=8.3 Hz, 1H), 7.86-7.78 (m, 1H), 7.57-7.47 (m, 3H), 7.42 (d, J=7.0 Hz, 1H), 5.66 (dd, J=8.6, 1.5 Hz, 1H), 5.64 (s, 1H), 4.50 (d, J=17.3 Hz, 1H), 4.41 (d, J=17.3 Hz, 1H), 3.98 (dd, J=11.9, 8.6 Hz, 1H), 3.77 (dd, J=11.9, 1.6 Hz, 1H), 3.69 (p, J=6.5 Hz, 1H), 1.34 (t, J=6.1 Hz, 6H).

Intermediates

The following intermediates were prepared as described in this document unless stated otherwise, and used in the synthesis of the compounds of the present disclosure.

Intermediate 1

(3R)-7-Methoxy-6-[(1-naphthyl)methyl]-4-oxo-1-thia-3a-aza-3-indancarboxylic acid

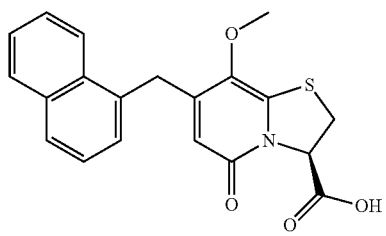 [SMILES: COc1c(Cc2cccc3ccccc23)cc(=O)n2c1SC[C@H]2C(=O)O]

¹H-NMR, 400 MHz, (DMSO) δ 3.60 (dd, J=1.7, 11.9 Hz, 1H), 3.70 (s, 3H), 3.91 (dd, J=8.9, 11.9 Hz, 1H), 4.30 (dd, J=16.8, 22.3 Hz, 2H), 5.35 (dd, J=1.7, 8.9 Hz, 1H), 5.37-5.38 (m, 1H), 7.41-7.45 (m, 1H), 7.48-7.57 (m, 3H), 7.85-7.99 (m, 3H), 13.43 (br s, 1H).

Intermediate 2

(3R)-7-Hydroxy-6-[(1-naphthyl)methyl]-4-oxo-1-thia-3a-aza-3-indancarboxylic acid

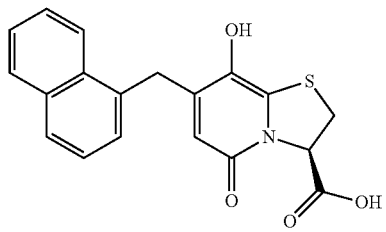 [SMILES: O=C(O)[C@@H]1CSc2c(O)c(Cc3cccc4ccccc34)cc(=O)n21]

¹H-NMR, 400 MHz, (DMSO) δ 3.53 (dd, J=1.6, 11.9 Hz, 1H), 3.83 (dd, J=8.9, 11.9 Hz, 1H), 4.26 (dd, J=16.9, 34.6 Hz, 2H), 5.27 (s, 1H), 5.33 (dd, J=1.6, 8.9 Hz, 1H), 7.41 (d, J=6.7 Hz, 1H), 7.46-7.57 (m, 3H), 7.84-7.99 (m, 3H), 8.56 (s, 1H), 13.32 (br s, 1H).

Intermediate 3

(3R)-7-Methoxy-4-oxo-6-[(2,3-xylyl)methyl]-1-thia-3a-aza-3-indancarboxylic acid

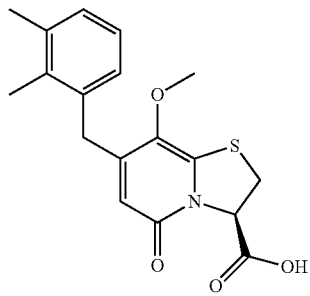 [SMILES: COc1c(Cc2cccc(C)c2C)cc(=O)n2c1SC[C@H]2C(=O)O]

¹H-NMR, 400 MHz, (DMSO) δ 2.07 (s, 3H), 2.26 (s, 3H), 3.60 (dd, J=1.7, 11.9 Hz, 1H), 3.66 (s, 3H), 3.84 (s, 2H), 3.90 (dd, J=8.9, 11.9 Hz, 1H), 5.32-5.34 (m, 1H), 5.37 (dd, J=1.7, 8.9 Hz, 1H), 6.98-7.12 (m, 3H), 13.45 (br s, 1H).

Intermediate 4

(3R)-5-Amino-7-methoxy-4-oxo-6-[(2,3-xylyl)methyl]-1-thia-3a-aza-3-indancarboxylic acid

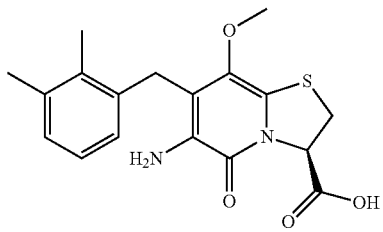 [SMILES: COc1c(Cc2cccc(C)c2C)c(N)c(=O)n2c1SC[C@H]2C(=O)O]

¹H-NMR, 400 MHz, (DMSO) δ 2.25 (s, 3H), 2.27 (s, 3H), 3.38 (s, 3H), 3.55 (dd, J=1.6, 11.9 Hz, 1H), 3.75 (dd, J=16.3, 21.3 Hz, 2H), 3.85 (dd, J=8.5, 11.9 Hz, 1H), 5.48 (dd, J=1.6, 8.5 Hz, 1H), 6.63 (dd, J=7.4 Hz, 1H), 6.90-7.02 (m, 2H).

Intermediate 5

7-Cyclopropyl-4-oxo-6-[(2,3-xylyloxy)methyl]-1,3a-diaza-3-indancarboxylic acid

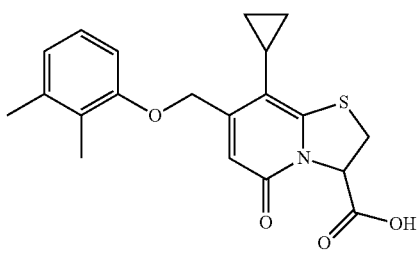 [SMILES: Cc1cccc(OCc2cc(=O)n3c(c2C2CC2)SCC3C(=O)O)c1C]

¹H NMR (400 MHz, DMSO-d₆) δ=0.52-0.59 (m, 1H), 0.63-0.70 (m, 1H), 0.81-0.92 (m, 2H), 1.64-1.73 (m, 1H), 3.02 (s, 3H), 3.04 (s, 3H), 3.53 (dd, J=1.6, 11.9 Hz, 1H), 3.81 (dd, J=9.2, 11.9 Hz, 1H), 5.14 (s, 2H), 5.42 (dd, J=1.6, 9.1 Hz, 1H), 6.20 (s, 1H), 6.78-6.84 (m, 2H), 7.02-7.09 (m, 1H), 13.41 (br s, 1H).

Intermediate 6

(3R)-7-(Methoxycarbonylamino)-6-[(1-naphthyl)methyl]-4-oxo-1-thia-3a-aza-3-indancarboxylic acid

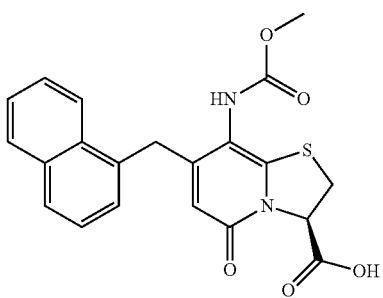 [SMILES: COC(=O)Nc1c(Cc2cccc3ccccc23)cc(=O)n2c1SC[C@H]2C(=O)O]

¹H NMR (400 MHz, Methanol-d₄) δ 7.96-7.86 (m, 2H), 7.82 (d, J=8.2 Hz, 1H), 7.52-7.43 (m, 3H), 7.39 (d, J=6.9 Hz, 1H), 5.49 (s, 1H), 5.38 (dd, J=8.6, 1.6 Hz, 1H), 4.23 (s, 2H), 3.83 (dd, J=11.4, 8.6 Hz, 1H), 3.74 (s, br, 3H), 3.63 (dd, J=11.4, 1.6 Hz, 1H).

Intermediate 7

(3R)-7-Acetylamino-6-[(1-naphthyl)methyl]-4-oxo-1-thia-3a-aza-3-indancarboxylic acid

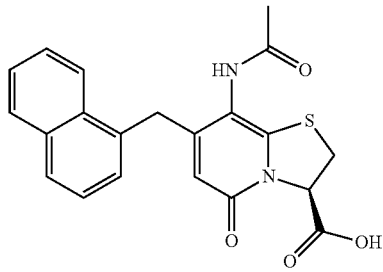 [SMILES: CC(=O)Nc1c(Cc2cccc3ccccc23)cc(=O)n2c1SC[C@H]2C(=O)O]

¹H NMR (400 MHz, Methanol-d₄) δ 7.95-7.86 (m, 2H), 7.82 (d, J=8.2 Hz, 1H), 7.52-7.43 (m, 3H), 7.37 (d, J=6.5 Hz, 1H), 5.38 (dd, J=8.6, 1.6 Hz, 1H), 4.20 (s, 2H), 3.83 (dd, J=11.3, 8.6 Hz, 1H), 3.63 (dd, J=11.3, 1.7 Hz, 1H), 2.08 (s, 3H).

Intermediate 8

(3R)-7-(Methylsulfonylamino)-6-[(1-naphthyl)methyl]-4-oxo-1-thia-3a-aza-3-indancarboxylic acid

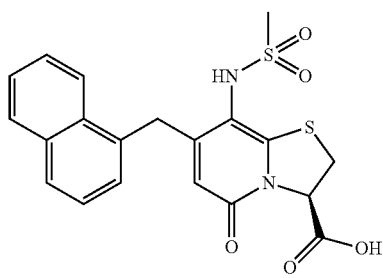 [SMILES: CS(=O)(=O)Nc1c(Cc2cccc3ccccc23)cc(=O)n2c1SC[C@H]2C(=O)O]

H NMR (400 MHz, Methanol-d₄) δ 7.99-7.71 (m, 3H), 7.56-7.29 (m, 4H), 5.56 (d, J=8.7 Hz, 1H), 5.39 (s, 1H), 4.56 (d, J=17.8 Hz, 1H), 4.45 (d, J=17.9 Hz, 1H), 3.96 (dd, J=11.9, 8.8 Hz, 1H), 3.69 (dd, J=11.8, 1.7 Hz, 1H), 3.24 (s, 3H).

Intermediate 9

(3R)-7-(Dimethylamino)-6-[(1-naphthyl)methyl]-4-oxo-1-thia-3a-aza-3-indancarboxylic acid

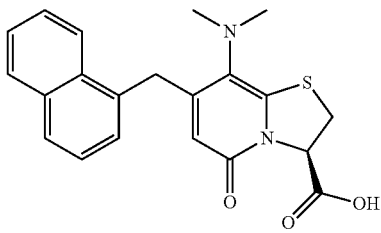 [SMILES: CN(C)c1c(Cc2cccc3ccccc23)cc(=O)n2c1SC[C@H]2C(=O)O]

¹H NMR (400 MHz, Methanol-d₄) δ 7.96-7.87 (m, 2H), 7.84 (d, J=8.2 Hz, 1H), 7.57-7.46 (m, 3H), 7.40 (d, J=6.9 Hz, 1H), 5.69 (s, 1H), 5.60 (d, J=8.7 Hz, 1H), 4.45 (s, 2H), 3.92 (dd, J=12.0, 8.8 Hz, 1H), 3.69 (d, J=12.0 Hz, 1H), 2.70 (s, 6H).

Intermediate 10

6-[(p-Chlorophenyl)methyl]-7-cyclopropyl-4-oxo-1,3a-diaza-3-indancarboxylic acid

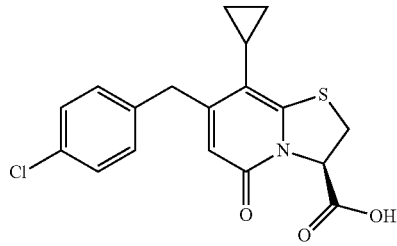 [SMILES: O=C(O)[C@@H]1CSc2c(C3CC3)c(Cc3ccc(Cl)cc3)cc(=O)n21]

Intermediate 17 was prepared according to WO2014185853.

Intermediate 11

7-Cyclopropyl-4-oxo-6-[(2,3-xylyl)methyl]-1,3a-diaza-3-indancarboxylic acid

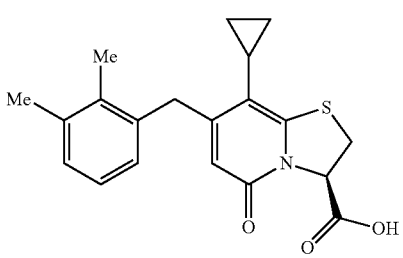 [SMILES: Cc1cccc(Cc2cc(=O)n3c(c2C2CC2)SC[C@H]3C(=O)O)c1C]

Intermediate 18 was prepared according to WO2014185853.

Intermediate 12

Methyl (3R)-7-methoxy-4-oxo-6-[(2,3-xylyloxy)methyl]-1-thia-3a-aza-3-indancarboxylate

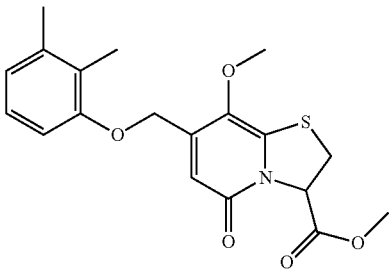 [SMILES: COC(=O)C1CSc2c(OC)c(COc3cccc(C)c3C)cc(=O)n21]

Intermediate 13

(3R)-7-Methoxy-4-oxo-6-[(2,3-xylyloxy)methyl]-1-thia-3a-aza-3-indancarboxylic acid

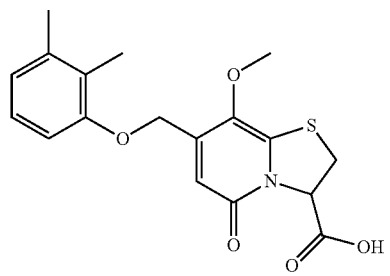 [SMILES: COc1c(COc2cccc(C)c2C)cc(=O)n2c1SCC2C(=O)O]

Intermediate 14

Methyl (3R)-7-chloro-6-[(1-naphthyl)methyl]-4-oxo-1-thia-3a-aza-3-indancarboxylate

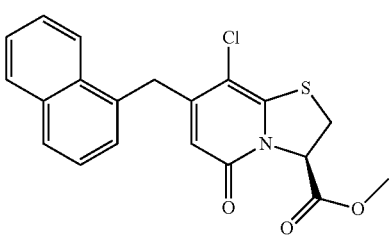 [SMILES: COC(=O)[C@@H]1CSc2c(Cl)c(Cc3cccc4ccccc34)cc(=O)n21]

$^1$H NMR (400 MHz, Chloroform-d) δ 7.91-7.86 (m, 1H), 7.81 (d, J=8.2 Hz, 1H), 7.78-7.72 (m, 1H), 7.59-7.37 (m, 3H), 7.31 (d, J=6.7 Hz, 1H), 5.69 (s, 1H), 5.60 (dd, J=8.5, 2.1 Hz, 1H), 4.36 (d, J=17.5 Hz, 1H), 4.24 (d, J=17.6 Hz, 1H), 3.80 (s, 3H), 3.79 (dd, J=11.9, 8.6 Hz, 1H), 3.59 (dd, J=11.8, 2.2 Hz, 1H).

Intermediate 15

(3R)-7-Chloro-6-[(1-naphthyl)methyl]-4-oxo-1-thia-3a-aza-3-indancarboxylic acid

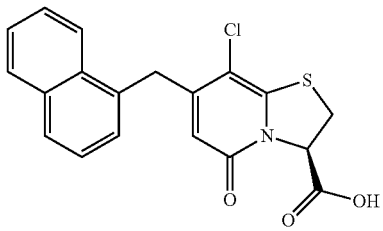 [SMILES: O=C(O)[C@@H]1CSc2c(Cl)c(Cc3cccc4ccccc34)cc(=O)n21]

$^1$H NMR (400 MHz, DMSO-d$_6$) δ 8.01-7.95 (m, 1H), 7.94-7.87 (m, 2H), 7.60-7.47 (m, 3H), 7.35 (d, J=7.1 Hz, 1H), 5.51 (s, 1H), 5.47 (dd, J=9.1, 1.7 Hz, 1H), 4.36 (d, J=17.2 Hz, 1H), 4.30 (d, J=17.1 Hz, 1H), 3.97 (dd, J=12.0, 9.1 Hz, 1H), 3.64 (dd, J=11.9, 1.7 Hz, 1H).

Intermediate 16

Methyl (3R)-7-methoxy-6-[(1-naphthyl)methyl]-4-oxo-1-thia-3a-aza-3-indancarboxylate

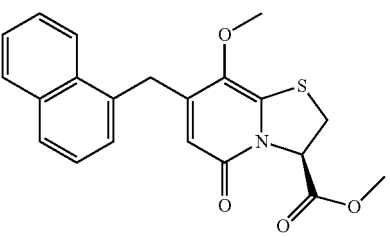 [SMILES: COC(=O)[C@@H]1CSc2c(OC)c(Cc3cccc4ccccc34)cc(=O)n21]

$^1$H-NMR (400 MHz, CDCl$_3$) δ 3.57 (dd, J=2.4, 12.0 Hz, 1H), 3.73 (dd, J=8.8, 11.6 Hz, 1H), 3.74 (s, 3H), 3.78 (s, 1H), 4.28 (q, J=17.2 Hz, 2H), 5.53 (dd, J=2.4, 8.4 Hz, 1H), 5.72 (s, 1H), 7.33 (d, J=6.8 Hz, 1H), 7.40-7.49 (m, 3H), 7.78 (d, J=8.4 Hz, 1H), 7.82-7.87 (m, 2H).

Intermediate 17

Methyl (3R)-6-(chloromethyl)-7-methoxy-4-oxo-1-thia-3a-aza-3-indancarboxylate

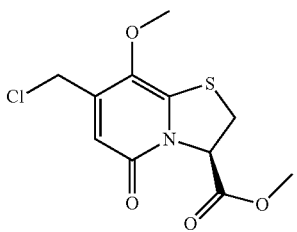 [SMILES: COC(=O)[C@@H]1CSc2c(OC)c(CCl)cc(=O)n21]

$^1$H-NMR, 400 MHz, (CDCl$_3$) δ 3.61 (dd, J=2.3, 11.7 Hz, 1H), 3.73-3.80 (m, 4H), 3.82 (s, 3H), 4.37-4.45 (m, 2H), 5.59 (dd, J=2.3, 8.4 Hz, 1H), 6.36-6.37 (m, 1H).

Intermediate 18

Methyl (3R)-7-methoxy-4-oxo-6-[(2,3-xylyl)methyl]-1-thia-3a-aza-3-indancarboxylate

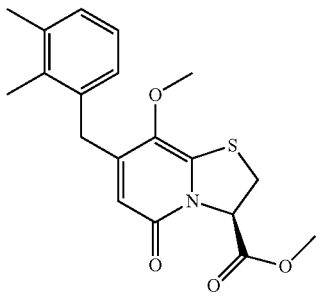

¹H-NMR, 400 MHz, (CDCl₃) δ 2.10 (s, 3H), 2.28 (s, 3H), 3.58 (dd, J=2.3, 11.7 Hz, 1H), 3.71 (s, 3H), 3.75 (dd, J=8.4, 11.7 Hz, 1H), 3.79-3.91 (m, 5H), 5.56 (dd, J=2.3, 8.4 Hz, 1H), 5.71 (t, J=1.1 Hz, 1H), 6.94-7.09 (m, 3H).

Intermediate 19

Methyl (3R)-7-hydroxy-6-[(1-naphthyl)methyl]-4-oxo-1-thia-3a-aza-3-indancarboxylate

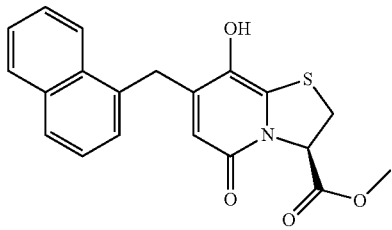 [SMILES: COC(=O)[C@@H]1CSc2c(O)c(Cc3cccc4ccccc34)cc(=O)n21]

¹H-NMR, 400 MHz, (DMSO) δ 3.56 (dd, J=2.0, 12.0 Hz, 1H), 3.68 (s, 3H), 3.86 (dd, J=8.9, 12.0 Hz, 1H), 4.27 (dd, J=17.0, 36.5 Hz, 2H), 5.29 (s, 1H), 5.44 (dd, J=2.0, 8.9 Hz, 1H), 7.39-7.56 (m, 4H), 7.85-7.99 (m, 3H), 8.61 (s, 1H).

Intermediate 20

Methyl (3R)-6-[(1-naphthyl)methyl]-4-oxo-7-(trifluoromethyl)-1-thia-3a-aza-3-indancarboxylate

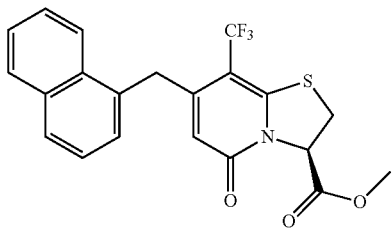 [SMILES: COC(=O)[C@@H]1CSc2c(C(F)(F)F)c(Cc3cccc4ccccc34)cc(=O)n21]

¹H-NMR, 400 MHz, (CDCl₃) δ 3.52 (dd, J=2.0, 11.9 Hz, 1H), 3.67 (dd, J=8.7, 11.9 Hz, 1H), 3.79 (m, 3H), 4.36 (dd, J=18.0, 39.5 Hz, 1H), 5.55-5.60 (m, 1H), 5.64 (s, 1H), 7.31-7.36 (m, 1H), 7.41-7.52 (m, 3H), 7.66-7.72 (m, 1H), 7.79-7.90 (m, 2H).

Intermediate 21

Methyl (3R)-5-amino-7-methoxy-4-oxo-6-[(2,3-xylyl)methyl]-1-thia-3a-aza-3-indancarboxylate

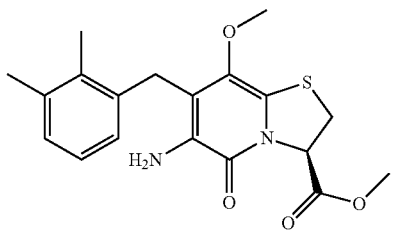

¹H-NMR, 400 MHz, (CDCl₃) δ 2.28 (s, 3H), 2.31 (s, 3H), 3.55 (s, 3H), 3.57 (dd, J=2.3, 11.7 Hz, 1H), 3.74 (dd, J=8.0, 11.7 Hz, 1H), 3.78-3.90 (m, 5H), 5.63 (dd, J=2.3, 8.0 Hz, 1H), 6.78-6.83 (m, 1H), 6.95-7.06 (m, 2H).

Intermediate 22

Methyl (3R)-7-(benzyloxycarbonylamino)-4-oxo-6-[(2,3-xylyl)methyl]-1-thia-3a-aza-3-indancarboxylate

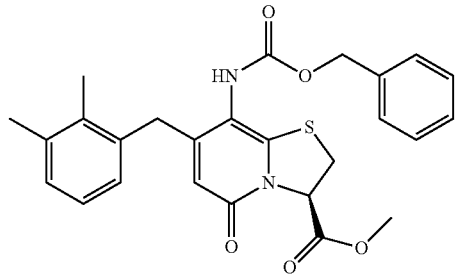 [SMILES: COC(=O)[C@@H]1CSc2c(NC(=O)OCc3ccccc3)c(Cc3cccc(C)c3C)cc(=O)n21]

¹H-NMR, 400 MHz, (CDCl₃) δ 2.06 (s, 3H), 2.27 (s, 3H), 3.50-3.85 (m, 7H), 5.19 (s, 2H), 5.59 (dd, J=2.3, 8.5 Hz, 1H), 5.72-5.82 (m, 2H), 6.80-7.10 (m, 3H), 7.28-7.43 (m, 5H).

Intermediate 23

Methyl (3R)-7-(benzyloxycarbonylamino)-6-[(4-methyl-1-naphthyl)methyl]-4-oxo-1-thia-3a-aza-3-indancarboxylate

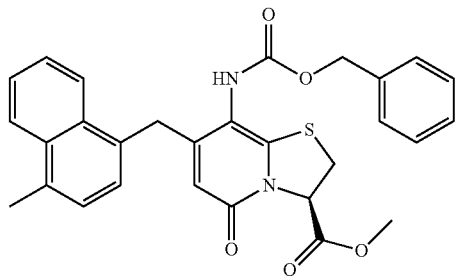 [SMILES: COC(=O)[C@@H]1CSc2c(NC(=O)OCc3ccccc3)c(Cc3ccc(C)c4ccccc34)cc(=O)n21]

¹H-NMR, 400 MHz, (CDCl₃) δ 2.68 (s, 3H), 3.54 (dd, J=2.1, 11.7 Hz, 1H), 3.66-3.83 (m, 4H), 4.15 (dd, J=17.2, 41.0 Hz, 2H), 5.17 (s, 2H), 5.57 (dd, J=2.1, 8.5 Hz, 1H), 5.67-5.90 (m, 2H), 7.05-7.25 (m, 2H), 7.28-7.58 (m, 7H), 7.76-7.90 (m, 1H), 8.02 (d, J=8.2 Hz, 1H).

Intermediate 24

Methyl (3R)-7-amino-6-[(1-naphthyl)methyl]-4-oxo-1-thia-3a-aza-3-indancarboxylate

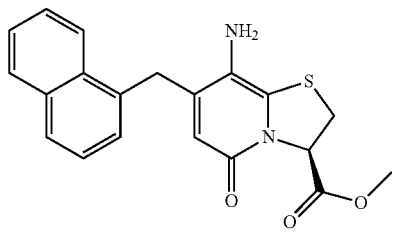 [SMILES: COC(=O)[C@@H]1CSc2c(N)c(Cc3cccc4ccccc34)cc(=O)n21]

¹H NMR (400 MHz, Methanol-d₄) δ 7.96-7.93 (m, 1H), 7.91 (d, J=8.3 Hz, 1H), 7.87-7.77 (m, 1H), 7.61-7.46 (m, 3H), 7.42 (d, J=7.0 Hz, 1H), 5.78 (dd, J=8.7, 1.7 Hz, 1H), 5.62 (s, 1H), 4.43 (s, 2H), 4.08 (dd, J=12.1, 8.7 Hz, 1H), 3.90 (dd, J=12.1, 1.7 Hz, 1H), 3.79 (s, 3H).

Intermediate 25

Methyl 7-cyclopropyl-4-oxo-6-[(2,3-xylyloxy)methyl]-1,3a-diaza-3-indancarboxylate

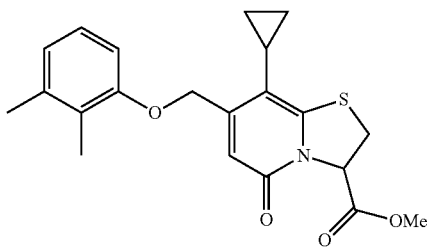 [SMILES: COC(=O)C1CSc2c(C3CC3)c(COc3cccc(C)c3C)cc(=O)n21]

¹H NMR (400 MHz, CDCl₃) δ=0.62-0.71 (m, 2H), 0.86-0.99 (m, 2H), 1.58-1.67 (m, 1H), 2.23 (s, 3H), 2.29 (s, 3H), 3.52 (dd, J=2.3, 11.7 Hz, 1H), 3.67 (dd, J=8.6, 11.7 Hz, 1H), 3.80 (s, 3H), 5.02-5.11 (m, 2H), 5.61 (dd, J=2.3, 8.5 Hz), 6.58-6.59 (m, 1H), 6.68-6.71 (m, 1H), 6.79-6.83 (m, 1H), 7.02-7.07 (m, 1H).

Intermediate 26

Methyl (4R)-2-(methoxymethyl)Δ²-1,3-thiazoline-4-carboxylate

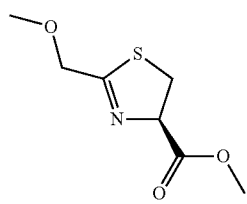

¹H-NMR, 400 MHz, (CDCl₃) δ 3.43 (s, 3H), 3.55 (dABq, J=9.3, 15.5 Hz, 2H), 3.81 (s, 3H), 4.28-4.37 (m, 2H), 5.13 (tt, J=9.3, Hz, 1H).

Intermediate 27

Methyl (4R)-2-(2,2,2-trifluoroethyl)Δ²-1,3-thiazoline-4-carboxylate

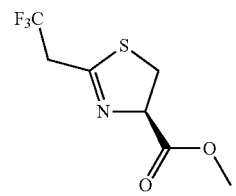

¹H-NMR, 400 MHz, (CDCl₃) δ 3.32-3.50 (m, 2H), 3.59-3.75 (m, 2H), 3.83 (s, 3H), 5.10-5.18 (m, 1H).

Intermediate 28

Methyl (4R)-2-[(methylsulfonyl)methyl]Δ²-1,3-thiazoline-4-carboxylate

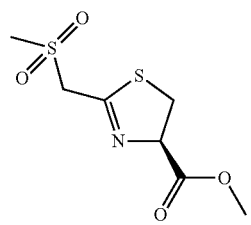

¹H-NMR, 400 MHz, (CDCl₃) δ 3.10 (s, 3H), 3.65-3.76 (m, 2H), 3.82 (s, 3H), 4.2 (s, 2H), 5.23 (t, J=9.0 Hz, 1H).

Intermediate 29

Methyl (4R)-2-[(benzyloxycarbonylamino)methyl]Δ²-1,3-thiazoline-4-carboxylate

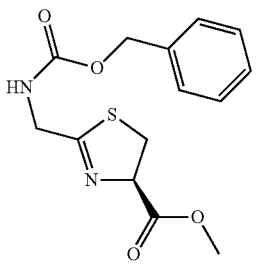 [SMILES: COC(=O)[C@@H]1CSC(CNC(=O)OCc2ccccc2)=N1]

¹H NMR (400 MHz, Chloroform-d) δ 7.41-7.28 (m, 5H), 5.48 (s, 1H), 5.14 (s, 2H), 5.14-5.04 (m, 1H), 4.25 (d, J=5.6 Hz, 2H), 3.81 (s, 3H), 3.70-3.41 (m, 2H).

Intermediate 30

5-[1-Hydroxy-2-(2,3-xylyl)ethylidene]-2,2-dimethyl-1,3-dioxane-4,6-dione

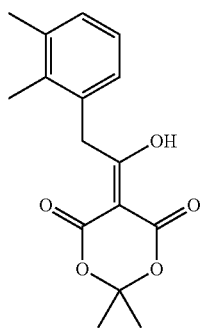 [SMILES: Cc1cccc(CC(O)=C2C(=O)OC(C)(C)OC2=O)c1C]

¹H-NMR, 400 MHz, (CDCl₃) δ 1.76 (s, 6H), 2.20 (s, 3H), 2.31 (s, 3H), 4.53 (s, 2H), 7.02-7.14 (m, 3H).

Intermediate 31

5-(2-Chloro-1-hydroxyethylidene)-2,2-dimethyl-1,3-dioxane-4,6-dione

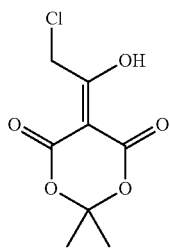

¹H-NMR, 400 MHz, (CDCl₃) δ 1.76 (s, 6H), 4.88 (s, 2H).

Intermediate 32

5-[1-Hydroxy-2-(1-naphthyl)ethylidene]-2,2-dimethyl-1,3-dioxane-4,6-dione

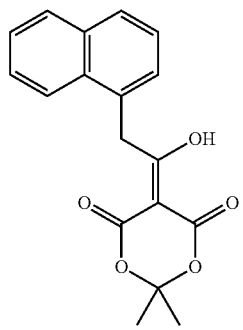 [SMILES: CC1(C)OC(=O)C(=C(O)Cc2cccc3ccccc23)C(=O)O1]

Intermediate 40 was prepared in accordance with Yamamoto, Y.; Watanabe, Y.; Ohnishi, S. *Chem. Pharm. Bull.* 1987, 35, 1860-1870.

Materials and Methods

Cell Culture, *C. trachomatis* Infections, and Determination of *C. trachomatis* Infectivity.

HeLa cells were infected with *C. trachomatis* serovar LGV-L2 at an MOI of 0.3. At 1 hpi, RPMI media containing the different dilutions of the tested compounds in DMSO were added. The different compounds were dissolved to 20 mM in DMSO and were then diluted with RPMI media to be added at 2.5 to 100 μM. After 44-48 h incubation, the cells were osmotically lysed by the addition of cold sterile distilled water to release infectious EB progeny. 5×SPG was added to equalize the osmotic pressure to a 1×SPG isotonic condition. An equal amount of HBSS (Hanks balanced salt solution) (Gibco/Invitrogen) was added to the lysate (yielding a 1:1 dilution) and 10-fold serial dilutions of the resulting mixture was used to infect fresh HeLa cells. At 1 hpi, the inoculum was replaced with RPMI media and the infection allowed to progress for 44-48 hours before fixation and staining. Fixation was performed by adding methanol for 5 minutes and the cells were subsequently washed with phosphate buffered saline (PBS). The chlamydial inclusions were stained by a primary rabbit anti-*Chlamydia* antibody (generated in-house) and a secondary donkey anti-rabbit FITC-labelled antibody (Jackson ImmunoResearch). The DNA of the cells and *Chlamydia* was stained by the addition of DAPI. The stained cells were analyzed by an ArrayScan automated scanner (ArrayScan VTI HCS, Thermo Scientific). Data were presented as the relative numbers of IFUs in treated infections compared to the numbers of IFUs in DMSO-treated control infections.

Biological Data

The compounds of Examples 1-33 were tested for inhibition of infectious *Chlamydia* progenies at concentrations of 2.5 μM, 10 μM, 50 μM and 100 μM. In this document μM stands for micromolar. The compounds of the present disclosure were considered to have antibacterial activity if they provided 50% or more inhibition of infectious *Chlamydia* progenies using at least one of the tested concentrations in Table 1.

TABLE 1

| Example number | % Inhibition of infectious Chlamydia progenies | | | |
|---|---|---|---|---|
| | 100 uM | 50 uM | 10 uM | 2.5 uM |
| 1 | | | | 100 |
| 2 | | | 100 | 96 |
| 3 | | | 100 | 95 |
| 4 | | | 100 | 99 |
| 5 | | | 100 | 100 |
| 6 | | | 100 | 63 |
| 7 | | | 100 | 90 |
| 8 | | | 100 | 87 |
| 9 | | | 100 | 89 |
| 10 | | | 98 | 88 |
| 11 | | | 100 | 97 |
| 12 | | | 100 | 98 |
| 13 | | | 100 | 75 |
| 14 | | | 100 | 76 |
| 15 | | | 100 | 84 |
| 16 | | | 100 | 81 |
| 17 | | | 100 | 79 |
| 18 | | | 12 | 46 |
| 19 | | | | 100 |
| 20 | | | | 99 |
| 21 | | | | 99 |
| 22 | | | 100 | 98 |
| 23 | | 98 | 98 | |
| 24 | | 99 | 98 | |
| 25 | | 97 | 97 | |

TABLE 1-continued

| Example number | % Inhibition of infectious Chlamydia progenies | | | |
|---|---|---|---|---|
| | 100 uM | 50 uM | 10 uM | 2.5 uM |
| 26 | | 87 | 54 | |
| 27 | | 98 | 96 | |
| 28 | 56 | | | |
| 29 | 56 | | | |
| 30 | 90 | 67 | | |
| 31 | 86 | 29 | | |
| 32 | 99 | 91 | | |
| 33 | 50 | | | |

The invention claimed is:

1. A compound of Formula I

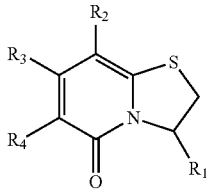

or a pharmaceutically acceptable salt thereof, wherein $R_1$ is selected from the group consisting of
a) $C(O)NR_5R_6$,
b) $C(O)OH$,
c) $C(O)SO_2R_8$, and
d)

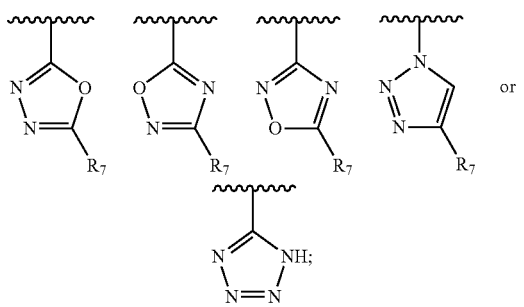

$R_2$ is selected from the group consisting of
a) OH,
b) $NZ_1Z_2$,
c) $C_1$-$C_4$alkoxy substituted with 0, 1, 2 or 3 substituents independently selected from the group consisting of F and Cl,
d) cyclopropoxy, cyclopropylmethoxy, phenyloxy, 2-pyridinyloxy or 4-pyridinyloxy each independently substituted with 0, 1, 2 or 3 substituents selected from the group consisting of F, Cl, methyl, ethyl, n-propyl, isopropyl, trifluoromethyl, methoxy, $CH_3SO_2O$ and phenylSO$_2$O,
e) $C_1$-$C_3$alkylthio, $C_1$-$C_3$alkylS(O)$, $C_1$-$C_3$alkylS(O)$_2$, phenylthio, phenylS(O) or phenylS(O)$_2$ each independently substituted with 0, 1, 2 or 3 substituents selected from the group consisting of F, Cl, methoxy, methyl and trifluoromethyl,
f) 2-pyridinylS(O)$_2$ substituted with 0, 1 or 2 substituents in positions 3, 4 or 5 independently selected from the group consisting of F, Cl, methoxy, methyl and trifluoromethyl,
g) 4-pyridinylS(O)$_2$ substituted with 0, 1 or 2 substituents in positions 2, 3 or 5 independently selected from the group consisting of F, Cl, methoxy, methyl and trifluoromethyl,
h) Cl or F,
and
i) $CF_3$;

$R_3$ is selected from the group consisting of
a) $CX_1X_2$phenyl, $CH_2$Ophenyl, $CX_1X_2$-(2)-pyridyl, $CX_1X_2$-(3)-pyridyl and $CX_1X_2$-(4)-pyridyl, each independently substituted with 0, 1, 2 or 3 substituents selected from the group consisting of F, Cl, methoxy, trifluoromethyl and methyl,
b) 1,3-dioxa-5-indanyl-methylene,
c) 1-naphtyl-methylene or 1-naphtyl-4-methyl-methylene,
and
d) 7-thiabicyclo[4.3.0]nona-1,3,5,8-tetraen-9-yl-methylene;

$R_4$ is selected from the group consisting of:
a) hydrogen,
and
b) $NY_1Y_2$;
and in the above definitions $R_5$ represents hydrogen or $C_1$-$C_6$alkyl,
or
$R_5$ represents phenyl, 2-pyridinyl or 4-pyridinyl each independently substituted with 0, 1, 2 or 3 substituents selected from the group consisting of F, Cl, methoxy, methyl and trifluoromethyl;

$R_6$ represents hydrogen, $C_1$-$C_4$alkyl or $C_1$-$C_6$cycloalkyl;

$R_7$ represents phenyl or 2-pyridinyl each independently substituted with 0, 1 or 2 substituents selected from the group consisting of F, Cl, methoxy, methyl and trifluoromethyl;

$R_8$ represents $C_1$-$C_3$alkyl, phenyl, 2-pyridinyl or 4-pyridinyl each independently substituted with 0, 1 or 2 substituents selected from the group consisting of F, Cl, methoxy, methyl and trifluoromethyl;

$X_1$ and $X_2$ each independently represents hydrogen, OH, halogen, oxo or $NH_2$;

$Y_1$ and $Y_2$ each independently represents hydrogen, methyl or $C(O)CH_3$, $CH_3S(O)_2$ or $Y_1$ and $Y_2$ together form $CH_2CH_2CH_2CH_2$ or $CH_2CH_2CH_2CH_2CH_2$;

$Z_1$ and $Z_2$ each independently represents hydrogen, $C_1$-$C_4$alkyl, $C_3$-$C_5$cycloalkyl, $C(O)CH_3$, $C(O)OCH_3$, $CH_3S(O)_2$ or phenylS(O)$_2$, or $Z_1$ and $Z_2$ together form $CH_2CH_2CH_2$, $CH_2CH_2CH_2CH_2$ or $CH_2CH_2CH_2CH_2CH_2$;

with the proviso that the compound of Formula (I) is not (3R)-7-methoxy-6-[(1-naphthyl)methyl]-4-oxo-1-thia-3a-aza-3-indancarboxylic acid, (3R)-6-[(1,3-dioxa-5-indanyl)methyl]-7-methoxy-4-oxo-1-thia-3a-aza-3-indancarboxylic acid or (3R)-7-methoxy-4-oxo-6-{(7-thiabicyclo[4.3.0]nona-1,3,5,8-tetraen-9-yl)methyl}-1-thia-3a-aza-3-indancarboxylic acid.

2. The compound according to claim 1, or a pharmaceutically acceptable salt thereof, which is a compound of Formula Ia Formula Ia

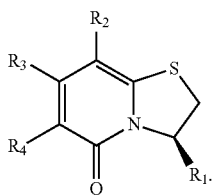

3. The compound according to claim 1, or a pharmaceutically acceptable salt thereof, wherein $R_1$ is $C(O)NR_5R_6$.

4. The compound according to claim 3, or a pharmaceutically acceptable salt thereof, wherein $R_5$ is hydrogen, and $R_6$ is phenyl or 5-chloro-2-pyridyl.

5. The compound according to claim 1, or a pharmaceutically acceptable salt thereof, wherein $R_1$ is C(O)OH.

6. The compound according to claim 1, or a pharmaceutically acceptable salt thereof, wherein $R_1$ is $C(O)SO_2R_8$.

7. The compound according to claim 1, or a pharmaceutically acceptable salt thereof, wherein $R_1$ is

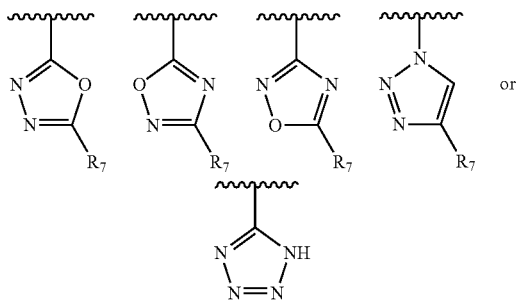

in which $R_7$ is phenyl or 2-pyridinyl each independently substituted with 0, 1 or 2 substituents independently selected from the group consisting of F, Cl, methoxy, methyl and trifluoromethyl.

8. The compound according to claim 7, or a pharmaceutically acceptable salt thereof, wherein $R_7$ is phenyl.

9. The compound according to claim 1, or a pharmaceutically acceptable salt thereof, wherein $R_2$ is OH.

10. The compound according to claim 1, or a pharmaceutically acceptable salt thereof, wherein $R_2$ is $NZ_1Z_2$.

11. The compound according to claim 1, or a pharmaceutically acceptable salt thereof, wherein $R_2$ is cyclopropoxy, phenyloxy, 2-pyridinyloxy or 4-pyridinyloxy each independently substituted with 0, 1, 2 or 3 substituents selected from the group consisting of F, Cl, methyl, ethyl, n-propyl, isopropyl, trifluoromethyl, methoxy, $CH_3SO_2O$ and phenylSO$_2$O.

12. The compound according to claim 1, or a pharmaceutically acceptable salt thereof, wherein $R_2$ is $C_1$-$C_3$alkylthio, $C_1$-$C_3$alkylS(O), $C_1$-$C_3$alkylS(O)$_2$, phenylthio, phenylS(O) or phenylS(O)$_2$ each independently substituted with 0, 1, 2 or 3 substituents selected from the group consisting of F, Cl, methoxy, methyl and trifluoromethyl.

13. The compound according to claim 1, or a pharmaceutically acceptable salt thereof, wherein $R_2$ is 2-pyridinylS(O)$_2$ substituted with 0, 1 or 2 substituents in positions 3, 4 or 5 independently selected from the group consisting of F, Cl, methoxy, methyl and trifluoromethyl.

14. The compound according to claim 1, or a pharmaceutically acceptable salt thereof, wherein $R_2$ is 4-pyridinylS(O)$_2$ substituted with 0, 1 or 2 substituents in positions 3, 4 or 5 independently selected from the group consisting of F, Cl, methoxy, methyl and trifluoromethyl.

15. The compound according to claim 1, or a pharmaceutically acceptable salt thereof, wherein $R_2$ is $C_1$-$C_4$alkoxy independently substituted with 0, 1, 2 or 3 substituents from the group consisting of F and Cl.

16. The compound according to claim 1, or a pharmaceutically acceptable salt thereof, wherein $R_2$ is selected from the group consisting of methoxy, ethoxy, cyclopropoxy, trifluoromethoxy, 2,2,2-trifluoroethoxy,N(CH$_3$)$_2$, $CH_3SO_2O$, PhSO$_2$O, methylthio, methylS(O), methylS(O)$_2$, phenylthio, phenylS(O), phenylS(O)$_2$, NHS(O)$_2$Me, NHS(O)$_2$Me and NHC(O)CH$_3$.

17. The compound according to claim 1, or a pharmaceutically acceptable salt thereof, wherein $R_3$ is selected from the group consisting of 2,3-xylylmethylene, 2,3-xyly-loxymethylene, 1-naphtylmethylene, 1-naphtyloxymethylene, 1,3-dioxa-5-indanyl-methylene, 7-thiabicyclo[4.3.0]nona-1,3,5,8-tetraen-9-yl-methylene, o-tolyl-methylene, 5-quinolyl-methylene and p-chlorophenyl-methylene.

18. The compound according to claim 1, or a pharmaceutically acceptable salt thereof, wherein $R_4$ is hydrogen, $NH_2$, or NHC(O)CH$_3$.

19. The compound according to claim 1, which is selected from:
 {(3R)-7-Methoxy-6-[(1-naphthyl)methyl]-4-oxo-1-thia-3a-aza-3-indanyl}anilinoformaldehyde;
 {(3R)-7-Methoxy-6-[(1-naphthyl)methyl]-4-oxo-1-thia-3a-aza-3-indanyl}(p-toluidino)formaldehyde;
 {(3R)-7-Methoxy-4-oxo-6-[(2,3-xylyl)methyl]-1-thia-3a-aza-3-indanyl}anilinoformaldehyde;
 {(3R)-7-Methoxy-4-oxo-6-[(2,3-xylyl)methyl]-1-thia-3a-aza-3-indanyl}(3-fluoro-5-toluidino)formaldehyde;
 {(3R)-7-Methoxy-4-oxo-6-[(2,3-xylyl)methyl]-1-thia-3a-aza-3-indanyl}(p-toluidino)formaldehyde;
 {(3R)-5-Amino-7-methoxy-6-[(1-naphthyl)methyl]-4-oxo-1-thia-3a-aza-3-indanyl}anilinoformaldehyde;
 {(3R)-5-Amino-7-methoxy-4-oxo-6-[(2,3-xylyl)methyl]-1-thia-3a-aza-3-indanyl}(p-toluidino)formaldehyde;
 {(3R)-5-Amino-7-methoxy-4-oxo-6-[(2,3-xylyl)methyl]-1-thia-3a-aza-3-indanyl}(3-fluoro-5-toluidino)formaldehyde;
 {(3R)-5-Amino-7-methoxy-6-[(1-naphthyl)methyl]-4-oxo-1-thia-3a-aza-3-indanyl}(p-toluidino)formaldehyde;
 {(3R)-7-Hydroxy-6-[(1-naphthyl)methyl]-4-oxo-1-thia-3a-aza-3-indanyl}anilinoformaldehyde;
 {(3R)-7-Chloro-6-[(1-naphthyl)methyl]-4-oxo-1-thia-3a-aza-3-indanyl}anilinoformaldehyde;
 {(3R)-6-[(1-Naphthyl)methyl]-4-oxo-7-(trifluoromethyl)-1-thia-3a-aza-3-indanyl}anilinoformaldehyde;
 {(3R)-5-Amino-7-methoxy-4-oxo-6-[(2,3-xylyl)methyl]-1-thia-3a-aza-3-indanyl}anilinoformaldehyde;
 (3R)-5-Amino-7-methoxy-3-(3-phenyl-1,2,4-oxadiazol-5-yl)-6-[(2,3-xylyl)methyl]-1-thia-3a-aza-4-indanone;
 (3R)-7-Methoxy-3-(5-phenyl-1,3,4-oxadiazol-2-yl)-6-[(2,3-xylyl)methyl]-1-thia-3a-aza-4-indanone;
 (3R)-7-Methoxy-3-(3-phenyl-1,2,4-oxadiazol-5-yl)-6-[(2,3-xylyl)methyl]-1-thia-3a-aza-4-indanone;
 {(3R)-7-Methoxy-4-oxo-6-[(2,3-xylyloxy)methyl]-1-thia-3a-aza-3-indanyl}(5-chloro-2-pyridylamino)formaldehyde;
 {(3R)-7-Methoxy-4-oxo-6-[(2,3-xylyloxy)methyl]-1-thia-3a-aza-3-indanyl}(5-chloro-2-pyridylamino)formaldehyde;
 Anilino {7-(isopropyl amino)-6-[(1-naphthyl)methyl]-4-oxo-1-thia-3a-aza-3-indanyl}formaldehyde;

{(3R)-7-(Dimethylamino)-6-[(1-naphthyl)methyl]-4-oxo-1-thia-3a-aza-3-indanyl}anilinoformaldehyde;
Anilino {7-(methylsulfonylamino)-6-[(1-naphthyl)methyl]-4-oxo-1-thia-3a-aza-3-indanyl}formaldehyde;
1-13-Anilinocarbonyl-6-[(1-naphthyl)methyl]-4-oxo-1-thia-3a-aza-7-indanylaminol-1-ethanone;
{(3R)-7-(Methoxycarbonylamino)-6-[(1-naphthyl)methyl]-4-oxo-1-thia-3a-aza-3-indanyl}anilinoformaldehyde;
(3R)-7-(Cyclopropylmethoxy)-6-[(1-naphthyl)methyl]-4-oxo-1-thia-3a-aza-3-indancarboxylic acid;
(3R)-6-[(1-Naphthyl)methyl]-4-oxo-7-(trifluoromethyl)-1-thia-3a-aza-3-indancarboxylic acid;
(3R)-7-Isobutoxy-6-[(1-naphthyl)methyl]-4-oxo-1-thia-3a-aza-3-indancarboxylic acid;
(3R)-7-(Dimethylamino)-4-oxo-6-[(2,3-xylyl)methyl]-1-thia-3a-aza-3-indancarboxylic acid;
(3R)-7-(Dimethylamino)-6-[(4-methyl-1-naphthyl)methyl]-4-oxo-1-thia-3a-aza-3-indancarboxylic acid; and
(3R)-7-(Isopropylamino)-6-[(1-naphthyl)methyl]-4-oxo-1-thia-3a-aza-3-indancarboxylic acid;

or a pharmaceutically acceptable salt of any of the foregoing compounds.

20. A pharmaceutical composition comprising a therapeutically effective amount of a compound as defined in claim 1, or a pharmaceutically acceptable salt thereof, and a pharmaceutically acceptable adjuvant, diluent or carrier.

21. A method for treatment and/or alleviation of a bacterial infection comprising administering to a mammal in need thereof an effective amount of the compound according to claim 1, or a pharmaceutically acceptable salt thereof.

22. The method according to claim 21, wherein the bacterial infection is a *Chlamydia* infection.

23. The method of claim 21, wherein the mammal is a human.

* * * * *